(12) United States Patent
Salam et al.

(10) Patent No.: US 12,168,842 B2
(45) Date of Patent: Dec. 17, 2024

(54) MODIFIED CELLULOSE-BASED NATURAL BINDER FOR NONWOVEN FABRICS

(71) Applicant: Glatfelter Corporation, Charlotte, NC (US)

(72) Inventors: Abdus Salam, Harrisburg, NC (US); Timothy Kistemaker, Mooresville, NC (US); Kirk Stallsmith, Denver, NC (US); Mark A. Lemere, Hobart, WI (US)

(73) Assignee: Glatfelter Corporation, Charlotte, NC (US)

( * ) Notice: Subject to any disclaimer, the term of this patent is extended or adjusted under 35 U.S.C. 154(b) by 1069 days.

(21) Appl. No.: 16/963,586

(22) PCT Filed: Jan. 31, 2019

(86) PCT No.: PCT/US2019/016031
§ 371 (c)(1),
(2) Date: Jul. 21, 2020

(87) PCT Pub. No.: WO2019/152638
PCT Pub. Date: Aug. 8, 2019

(65) Prior Publication Data
US 2021/0054548 A1 Feb. 25, 2021

Related U.S. Application Data

(60) Provisional application No. 62/624,377, filed on Jan. 31, 2018.

(51) Int. Cl.
*D04H 1/587* (2012.01)
*C08L 1/28* (2006.01)

(52) U.S. Cl.
CPC .............. *D04H 1/587* (2013.01); *C08L 1/286* (2013.01); *C08L 2201/06* (2013.01); *C08L 2201/54* (2013.01)

(58) Field of Classification Search
CPC ...... D04H 1/587; D04H 1/641; A61K 8/0208; C08L 1/286; C08L 2201/06; C08L 2201/54
See application file for complete search history.

(56) References Cited

U.S. PATENT DOCUMENTS

| | | | |
|---|---|---|---|
| 3,621,847 A | 11/1971 | Roberson | |
| 2010/0330376 A1* | 12/2010 | Trksak | C08B 11/08 |
| | | | 428/533 |
| 2016/0051115 A1* | 2/2016 | Smith | A61K 8/0208 |
| | | | 15/104.93 |

FOREIGN PATENT DOCUMENTS

| | | | |
|---|---|---|---|
| EP | 0 801 172 A1 | 10/1997 | |
| EP | 0801172 A4 | 8/1998 | |
| GB | 2 513 124 A | 10/2014 | |
| GB | 2513124 B | 12/2018 | |
| JP | H11279915 | * 10/2005 | ............. A61F 13/84 |

OTHER PUBLICATIONS

International Search Report and Written Opinion mailed in International Application No. PCT/US2019/016031 dated Apr. 24, 2019.

* cited by examiner

*Primary Examiner* — Camie S Thompson
(74) *Attorney, Agent, or Firm* — Blank Rome LLP

(57) ABSTRACT

Aqueous cellulosic binder comprising modified cellulose (carboxymethylcellulose and/or sodium carboxymethylcellulose), water, and optionally binder modifier (crosslinking agent and/or wet strength agent); with a weight ratio of water:modified cellulose of 99.9:0.1 to 1,000:500, with a weight ratio of binder modifier:modified cellulose of 1:2 to 1:1,000; wherein crosslinking agent comprises carboxylic acid having two or more carboxyl groups; and wherein wet strength agent comprises a reactive functional group (halide, chloride, fluoride, hydroxyl). A method of making aqueous cellulosic binder comprising contacting modified cellulose with water to form modified cellulose solution; and optionally contacting modified cellulose solution with binder modifier to form aqueous cellulosic binder. A nonwoven fabric comprising fiber web (85-99.9 wt. %); and cured cellulosic binder (0.1-15 wt. %). An article formed from the nonwoven fabric. A method of making nonwoven fabric comprising forming fiber web; contacting web with aqueous cellulosic binder to form binder impregnated fiber web; and curing to form the nonwoven fabric.

17 Claims, No Drawings

MODIFIED CELLULOSE-BASED NATURAL BINDER FOR NONWOVEN FABRICS

This application is a national stage entry under 35 U.S.C. § 371 of PCT International Application No. PCT/US2019/016031, filed Jan. 31, 2019, and claims the benefit of U.S. Provisional Application No. 62/624,377 filed Jan. 31, 2018, the priority to all of which is claimed and the disclosures of all of which are incorporated herein by reference in their entireties.

TECHNICAL FIELD

The present disclosure relates to binder compositions for nonwovens, more specifically cellulose-based binders for nonwoven materials and methods of making and using same.

BACKGROUND

Nonwovens are generally used in a wide range of consumer and industrial products with diverse properties, including healthcare and surgical fabrics, wipes, absorbent hygiene products, apparel, home furnishings, construction, filtration, and engineering. A nonwoven material is a sheet of fibers, continuous filaments (e.g., fiber precursors), or chopped yarns of any nature or origin, that have been formed into a web by any means, and bonded together by any means, with the exception of weaving or knitting.

Some nonwoven fabrics have sufficient web strength after forming to be handled even if they are subsequently additionally bonded, for example when a bonding step is an integral part of the web-forming process, as in spun-bond and melt-blown nonwovens. Most other webs have relatively little strength as formed and may require an additional bonding step (e.g., chemical bonding) in order to make the nonwoven web suitable for its intended end use. Chemical bonding in nonwovens products normally refers to the use of latex binders, which have been in existence at least as long as most modern nonwovens themselves. A benefit of latex binders is their overall versatility and utility. However, latex binders are expensive and require the use of large volumes of binder to achieve the minimum target quality. Further, latex binders can raise environmental and health concerns pertaining to non-biodegradability, volatile organic compound emissions and formaldehyde formation. Another issue during nonwoven fabric manufacturing is a high dust level, which can be difficult to control with latex binders, potentially posing health, safety and environmental concerns. Thus, there is an ongoing need for the development of improved binder compositions for nonwovens.

BRIEF SUMMARY

Disclosed herein is an aqueous cellulosic binder comprising modified cellulose, water, and optionally a crosslinking agent; wherein the aqueous cellulosic binder is characterized by a weight ratio of water to modified cellulose of from about 99.9:0.1 to about 1,000:500; wherein, when the crosslinking agent is present, the aqueous cellulosic binder is characterized by a weight ratio of crosslinking agent to modified cellulose of from about 1:2 to about 1:1,000; wherein the modified cellulose comprises carboxymethylcellulose (CMC) and/or sodium carboxymethylcellulose (sodium CMC); and wherein the crosslinking agent comprises a carboxylic acid having two or more carboxyl groups.

Also disclosed herein is a cellulosic binder comprising modified cellulose and a crosslinking agent in a weight ratio of crosslinking agent to modified cellulose of from about 1:2 to about 1:1,000, wherein the modified cellulose comprises CMC and/or sodium CMC, and wherein the crosslinking agent comprises a carboxylic acid having two or more carboxyl groups.

Further disclosed herein is a cellulosic binder comprising modified cellulose and a wet strength agent in a weight ratio of wet strength agent to modified cellulose of from about 1:2 to about 1:1,000, wherein the modified cellulose comprises CMC and/or sodium CMC, and wherein the wet strength agent comprises at least one reactive functional group selected from the group consisting of a halide group, a chloride group, a fluoride group, a hydroxyl group, and combinations thereof.

Further disclosed herein is a method of making an aqueous cellulosic binder, the method comprising contacting modified cellulose with water, and optionally an electrolyte to form an aqueous cellulosic binder; wherein the modified cellulose comprises CMC and/or sodium CMC; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

Further disclosed herein is a method of making an aqueous cellulosic binder, the method comprising (a) contacting modified cellulose with water to form a modified cellulose solution, wherein the modified cellulose comprises CMC and/or sodium CMC; and (b) contacting at least a portion of the modified cellulose solution with a binder modifier to form the aqueous cellulosic binder; wherein the binder modifier comprises a crosslinking agent and/or a wet strength agent; wherein the crosslinking agent comprises a carboxylic acid having two or more carboxyl groups; wherein the wet strength agent comprises at least one reactive functional group selected from the group consisting of a halide group, a chloride group, a fluoride group, a hydroxyl group, and combinations thereof, and wherein the aqueous cellulosic binder is characterized by a weight ratio of binder modifier to modified cellulose of from about 1:2 to about 1:1,000.

Further disclosed herein is a method of making a nonwoven fabric, the method comprising (a) forming a plurality of fibers into a fiber web; (b) contacting at least a portion of the fiber web with an aqueous cellulosic binder to form a binder impregnated fiber web; wherein the aqueous cellulosic binder comprises modified cellulose, water, and optionally an electrolyte; wherein the aqueous cellulosic binder is characterized by a weight ratio of water to modified cellulose of from about 99.9:0.1 to about 1,000:500; wherein the modified cellulose comprises CMC and/or sodium CMC; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, and (c) curing the binder impregnated fiber web to form the nonwoven fabric.

Further disclosed herein is a method of making a nonwoven fabric, the method comprising (a) forming a plurality of fibers into a fiber web; (b) contacting at least a portion of the fiber web with an aqueous cellulosic binder to form a binder impregnated fiber web; wherein the aqueous cellulosic binder comprises modified cellulose, a binder modifier, and water; wherein the binder modifier comprises a crosslinking agent and/or a wet strength agent; wherein the aqueous cellulosic binder is characterized by a weight ratio of water to modified cellulose of from about 99.9:0.1 to about 1,000:500; wherein the aqueous cellulosic binder is characterized by a weight ratio of natural binder to modified cellulose of from about 1:2 to about 1:1,000; wherein the modified cellulose comprises CMC and/or sodium CMC; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof, and (c) curing the binder impregnated fiber web to form the nonwoven fabric.

Further disclosed herein is a nonwoven fabric comprising a fiber web in an amount of from about 85 wt. % to about 99.9 wt. %, based on the total weight of the nonwoven fabric; and a cured cellulosic binder in an amount of from about 0.1 wt. % to about 15 wt. %, based on the total weight of the nonwoven fabric; wherein the cured cellulosic binder comprises modified cellulose, optionally an electrolyte, and optionally a binder modifier; wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, wherein the binder modifier comprises a crosslinking agent and/or a wet strength agent; wherein, when the binder modifier is present, the cured cellulosic binder is characterized by a weight ratio of binder modifier to modified cellulose of from about 1:2 to about 1:1,000; wherein the modified cellulose comprises CMC and/or sodium CMC; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

Further disclosed herein is a nonwoven fibrous material chemically bound with a modified cellulose-based binder, wherein the modified cellulose-based binder comprises CMC and/or sodium CMC crosslinked with citric acid.

Further disclosed herein is an aqueous cellulosic binder comprising modified cellulose, water, and optionally an electrolyte; wherein the aqueous cellulosic binder is characterized by a weight ratio of water to modified cellulose of from about 99.9:0.1 to about 1,000:500; wherein, when the electrolyte is present, the aqueous cellulosic binder comprises the electrolyte in an amount of from about 0.1 wt. % to about 10 wt. %; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

Further disclosed herein is an aqueous cellulosic binder comprising modified cellulose, a binder modifier, and water; wherein the aqueous cellulosic binder is characterized by a weight ratio of water to modified cellulose of from about 99.9:0.1 to about 1,000:500; wherein the aqueous cellulosic binder is characterized by a weight ratio of binder modifier to modified cellulose of from about 1:2 to about 1:1,000; wherein the modified cellulose comprises CMC and/or sodium CMC; wherein the binder modifier comprises a crosslinking agent, a wet strength agent, or both a crosslinking agent and a wet strength agent; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

Further disclosed herein is a cellulosic binder comprising modified cellulose and a binder modifier in a weight ratio of binder modifier to modified cellulose of from about 1:2 to about 1:1,000; wherein the modified cellulose comprises CMC and/or sodium CMC; wherein the binder modifier comprises a crosslinking agent, a wet strength agent, or both a crosslinking agent and a wet strength agent; and wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

Further disclosed herein is a method of making an aqueous cellulosic binder, the method comprising (a) contacting modified cellulose with water to form a modified cellulose solution, wherein the modified cellulose comprises CMC and/or sodium CMC; and (b) contacting at least a portion of the modified cellulose solution with an electrolyte to form the aqueous cellulosic binder; wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, and wherein the aqueous cellulosic binder is characterized by a weight ratio of electrolyte to modified cellulose of from about 1:10 to about 1:1,000.

Further disclosed herein is a method of making an aqueous cellulosic binder, the method comprising (a) contacting modified cellulose with water to form a modified cellulose solution, wherein the modified cellulose comprises CMC and/or sodium CMC, and wherein the modified cellulose solution comprises the modified cellulose in an amount of from about 0.1 wt. % to about 50 wt. %; and (b) contacting at least a portion of the modified cellulose solution with a binder modifier to form the aqueous cellulosic binder; wherein the binder modifier comprises a crosslinking agent, a wet strength agent, or both a crosslinking agent and a wet strength agent; wherein the crosslinking agent comprises a carboxylic acid having two or more carboxyl groups; wherein the wet strength agent comprises at least one reactive functional group selected from the group consisting of a halide group, a chloride group, a fluoride group, a hydroxyl group, and combinations thereof, and wherein the aqueous cellulosic binder is characterized by a weight ratio of binder modifier to modified cellulose of from about 1:2 to about 1:1,000.

Further disclosed herein is a method of making a nonwoven fabric, the method comprising (a) forming a plurality of fibers into a fiber web; (b) contacting at least a portion of the fiber web with an aqueous cellulosic binder to form a binder impregnated fiber web; wherein the aqueous cellulosic binder comprises modified cellulose, water, and optionally an electrolyte; wherein the aqueous cellulosic binder is characterized by a weight ratio of water to modified cellulose of from about 99.9:0.1 to about 1,000:500; wherein, when the electrolyte is present, the aqueous cellulosic binder comprises the electrolyte in an amount of from about 0.1 wt. % to about 10 wt. %; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, and (c) curing the binder impregnated fiber web to form the nonwoven fabric, wherein the nonwoven fabric comprises a cured cellulosic binder, and wherein the cured cellulosic binder comprises at least a portion of the modified cellulose of the aqueous cellulosic binder and at least a portion of the binder modifier of the aqueous cellulosic binder.

Further disclosed herein is a method of making a nonwoven fabric, the method comprising (a) forming a plurality of fibers into a fiber web; (b) contacting at least a portion of the fiber web with an aqueous cellulosic binder to form a binder impregnated fiber web; wherein the aqueous cellulosic binder comprises modified cellulose, a binder modifier, and water; wherein the aqueous cellulosic binder is characterized by a weight ratio of water to modified cellulose of from about 99.9:0.1 to about 1,000:500; wherein the aqueous cellulosic binder is characterized by a weight ratio of binder modifier to modified cellulose of from about 1:2 to about 1:1,000; wherein the modified cellulose comprises CMC and/or sodium CMC; wherein the binder modifier comprises a crosslinking agent, a wet strength agent, or both a crosslinking agent and a wet strength agent; and wherein the crosslinking agent comprises a carboxylic acid having two or more carboxyl groups; wherein the wet strength agent comprises at least one reactive functional group selected from the group consisting of a halide group, a chloride group, a fluoride group, a hydroxyl group, and combinations thereof, and (c) curing the binder impregnated fiber web to form the nonwoven fabric, wherein the nonwoven fabric comprises a cured cellulosic binder, and wherein the cured cellulosic binder comprises at least a portion of the modified cellulose of the aqueous cellulosic binder and at least a portion of the binder modifier of the aqueous cellulosic binder.

Further disclosed herein is a nonwoven fabric comprising a fiber web in an amount of from about 85 wt. % to about 99.9 wt. %, based on the total weight of the nonwoven fabric, wherein the fiber web comprises natural fibers, synthetic fibers, or both natural fibers and synthetic fibers; and a cured cellulosic binder in an amount of from about 0.1 wt. % to about 15 wt. %, based on the total weight of the nonwoven fabric, wherein the cured cellulosic binder comprises modified cellulose and optionally an electrolyte, and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

Further disclosed herein is a nonwoven fabric comprising a fiber web in an amount of from about 85 wt. % to about 99.9 wt. %, based on the total weight of the nonwoven fabric, wherein the fiber web comprises natural fibers, synthetic fibers, or both natural fibers and synthetic fibers; and a cured cellulosic binder in an amount of from about 0.1 wt. % to about 15 wt. %, based on the total weight of the nonwoven fabric, wherein the cured cellulosic binder comprises modified cellulose and a binder modifier in a weight ratio of binder modifier to modified cellulose of from about 1:2 to about 1:1,000, wherein the modified cellulose comprises CMC and/or sodium CMC, wherein the binder modifier comprises a crosslinking agent, a wet strength agent, or both a crosslinking agent and a wet strength agent; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

DETAILED DESCRIPTION

Disclosed herein are cellulosic binder compositions and methods of making and using same. The cellulosic binder compositions can be a natural binder comprising modified cellulose, a binder modifier (e.g., crosslinking agent and/or wet strength agent), and optionally a softening agent and/or other additives. Further disclosed herein are methods of preparing natural cellulosic binder compositions, wherein the cellulosic binder compositions can be designed to improve (e.g., increase) various properties of nonwoven fabrics, such as dry strength, wet strength, oil wet strength, softness, water and mineral oil absorbency, water dispersibility, and the like, or combinations thereof.

In an aspect, the cellulosic binder composition can comprise modified cellulose, a crosslinking agent, and water, wherein the cellulosic binder composition is characterized by a weight ratio of water to modified cellulose of from about 99.9:0.1 to about 1,000:500, wherein the cellulosic binder composition is characterized by a weight ratio of crosslinking agent to modified cellulose of from about 1:2 to about 1:1,000, wherein the modified cellulose comprises carboxymethylcellulose (CMC) and/or sodium carboxymethylcellulose (sodium CMC), and wherein the crosslinking agent comprises a carboxylic acid having two or more carboxyl groups. In an aspect, the cellulosic binder composition is a sprayable aqueous solution.

In an aspect, the cellulosic binder composition can comprise modified cellulose, a wet strength agent, and water, wherein the cellulosic binder composition is characterized by a weight ratio of water to modified cellulose of from about 99.9:0.1 to about 1,000:500, wherein the cellulosic binder composition is characterized by a weight ratio of wet strength agent to modified cellulose of from about 1:2 to about 1:1,000, wherein the modified cellulose comprises CMC and/or sodium CMC, and wherein the wet strength agent comprises at least one reactive functional group selected from the group consisting of a halide group, a chloride group, a fluoride group, a hydroxyl group, and combinations thereof. In an aspect, the cellulosic binder composition is a sprayable aqueous solution.

In an aspect, a method of making an aqueous cellulosic binder can generally comprise contacting modified cellulose with water, and optionally an electrolyte to form an aqueous cellulosic binder; wherein the modified cellulose comprises CMC and/or sodium CMC; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

In an aspect, a method of making an aqueous cellulosic binder can generally comprise the steps of (a) contacting modified cellulose with water to form a modified cellulose solution, wherein the modified cellulose comprises CMC and/or sodium CMC; and (b) contacting at least a portion of the modified cellulose solution with a binder modifier to form the aqueous cellulosic binder; wherein the binder modifier comprises a crosslinking agent and/or a wet strength agent; wherein the crosslinking agent comprises a carboxylic acid having two or more carboxyl groups; wherein the wet strength agent comprises at least one reactive functional group selected from the group consisting of a halide group, a chloride group, a fluoride group, a hydroxyl group, and combinations thereof, and wherein the aqueous cellulosic binder is characterized by a weight ratio of binder modifier to modified cellulose of from about 1:2 to about 1:1,000.

Also disclosed herein are nonwoven fabrics and methods of making and using same. In an aspect, a nonwoven fabric can comprise a fiber web in an amount of from about 85 wt. % to about 99.9 wt. %, based on the total weight of the nonwoven fabric; and a cured cellulosic binder in an amount of from about 0.1 wt. % to about 15 wt. %, based on the total weight of the nonwoven fabric, wherein the cured cellulosic binder comprises modified cellulose and a crosslinking agent in a weight ratio of crosslinking agent to modified cellulose of from about 1:2 to about 1:1,000, wherein the modified cellulose comprises CMC and/or sodium CMC, and wherein the crosslinking agent comprises a carboxylic acid having two or more carboxyl groups. In an aspect, the fiber web can comprise cellulosic fibers, and can be biodegradable.

In an aspect, a method of making a nonwoven fabric can generally comprise the steps of (a) forming a plurality of fibers into a fiber web; (b) contacting at least a portion of the fiber web with an aqueous cellulosic binder to form a binder impregnated fiber web; wherein the aqueous cellulosic binder comprises modified cellulose, water, and optionally an electrolyte; wherein the aqueous cellulosic binder is characterized by a weight ratio of water to modified cellulose of from about 99.9:0.1 to about 1,000:500; wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, and wherein the modified cellulose comprises CMC and/or sodium CMC; and (c) curing the binder impregnated fiber web to form the nonwoven fabric. In such aspect, the method of making a nonwoven fabric can comprise an airlaid process.

In an aspect, a method of making a nonwoven fabric can generally comprise the steps of (a) forming a plurality of fibers into a fiber web; (b) contacting at least a portion of the fiber web with an aqueous cellulosic binder to form a binder impregnated fiber web; wherein the aqueous cellulosic binder comprises modified cellulose, a binder modifier, and water; wherein the binder modifier comprises a crosslinking agent and/or a wet strength agent; wherein the aqueous cellulosic binder is characterized by a weight ratio of water to modified cellulose of from about 99.9:0.1 to about 1,000:500; wherein the aqueous cellulosic binder is characterized by a weight ratio of natural binder to modified cellulose of from about 1:2 to about 1:1,000; wherein the modified cellulose comprises CMC and/or sodium CMC; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof, and (c) curing the binder impregnated fiber web to form the nonwoven fabric. In such aspect, the method of making a nonwoven fabric can comprise an airlaid process.

The terms used herein generally have their ordinary meanings in the art, within the context of this disclosure and in the specific context where each term is used. Certain terms are defined below to provide additional guidance in describing the compositions and methods of the current disclosure and how to make and use them.

As used in the specification and the appended claims, the singular forms "a," "an" and "the" include plural referents unless the context clearly dictates otherwise. Thus, for example, reference to "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, alternatively up to 10%, alternatively up to 5%, or alternatively up to 1% of a given value. Alternatively, particularly with respect to systems or processes, the term can mean within an order of magnitude, within 5-fold, and within 2-fold, of a value.

As used herein, the term "weight percent" (wt. %) is meant to refer to either (i) the quantity by weight of a constituent or component in a material as a percentage of the weight of the material; or (ii) to the quantity by weight of a constituent or component in a material as a percentage of the weight of the final nonwoven material or product.

The term "basis weight" as used herein refers to the quantity by weight of a compound over a given area. Examples of the units of measure include grams per square meter as identified by the acronym (gsm).

As used herein, the terms "gli," "g/in," and "G/in" refer to "grams per linear inch" or "gram force per inch." This refers to the width, not the length, of a test sample for tensile strength testing.

As used herein, "aqueous" means water and mixtures composed substantially of water.

As used herein, the terms "fiber," "fibrous" and the like are intended to encompass materials that have an elongated morphology exhibiting an aspect ratio (length to thickness) of greater than about 100, alternatively greater than about 500, alternatively greater than about 1,000, or alternatively greater than about 10,000.

In an aspect, a cellulosic binder as disclosed herein can comprise modified cellulose. In an aspect, the cellulosic binder as disclosed herein can comprise water (e.g., aqueous cellulosic binder). For purposes of the disclosure herein, the cellulosic binder comprising water can be referred to as "aqueous cellulosic binder."

In some aspects, the cellulosic binder can optionally comprise an electrolyte, as will be described in more detail later herein. In an aspect, an aqueous cellulosic binder can comprise modified cellulose, water, and optionally an electrolyte.

In other aspects, the cellulosic binder can comprise modified cellulose and a binder modifier, wherein the binder modifier can comprise a crosslinking agent and/or a wet strength agent, as will be described in more detail later herein. In an aspect, an aqueous cellulosic binder can comprise modified cellulose, water, and a crosslinking agent. In another aspect, an aqueous cellulosic binder can comprise modified cellulose, water, and a wet strength agent. In yet another aspect, an aqueous cellulosic binder can comprise modified cellulose, water, a crosslinking agent, and a wet strength agent.

In an aspect, the cellulosic binder can comprise modified cellulose, wherein the modified cellulose comprises CMC and/or sodium CMC. CMC and sodium CMC are cellulose derivatives (i.e., modified cellulose). Cellulose is a fibrous carbohydrate found in plants, and is the structural component of plant cell walls. Cellulose is considered the most abundant naturally occurring organic polymer on Earth; accounting for over half of all the carbon found in the plant kingdom. Cellulose is a polysaccharide, and is a linear polymer of glucose consisting of a linear chain of hundreds to thousands of D-glucose units that are linked by β-1,4-glycosidic linkages. Carboxymethylcellulose (CMC) is a chemically modified derivative of cellulose, and is generally formed by reaction of cellulose with alkali and chloroacetic acid. Each repeating glucose unit in CMC has three hydroxyl groups (—OH), each of which, and without wishing to be limited by theory, could be substituted with carboxymethyl groups (—$CH_2$—COOH) to form the corresponding carboxymethyl ethers (—O—$CH_2$—COOH). However, based on the cellulose starting material, and on the reaction conditions, only some of the hydroxyl groups in the cellulose polymer chain end up substituted with carboxymethyl groups, and the average number of hydroxyl groups substituted per glucose monomeric unit is known as the degree of substitution. The properties (e.g., solubility, viscosity) of the CMC are dependent upon the length of the polymeric chain, as well as upon the degree of substitution. Generally, CMC is commercially available with a degree of substitution of from about 0.3 to about 2, most commonly from about 0.6 to about 0.9. As will be appreciated by one of skill in the art, and with the help of this disclosure, and without wishing to be limited by theory, the pKa of CMC depends on the degree of substitution, and for the most commonly available CMC (e.g., degree of substitution from about 0.6 to about 0.9), the pKa is about 4-5, being similar to the pKa of acetic acid. Further, and as will be appreciated by one of skill in the art, and with the help of this disclosure, and without wishing to be limited by theory, depending on the pH of the solution used for obtaining the CMC, the CMC could be fully protonated (e.g., pH values below the pKa, such as a pH of 1-2); the CMC could be fully deprotonated, and as such it would be sodium CMC (e.g., pH values above the pKa, such as a pH of 7); or the CMC could be partially protonated and partially deprotonated (e.g., sodium salt) at pH values around the pKa. Sodium CMC comprise at least a portion of the carboxymethyl ether groups in sodium salt form (—O—$CH_2$—$COO^-Na^+$).

CMC and sodium CMC can be used in foods, cosmetics, and even in pharmaceutics, owing to being biocompatible, biodegradable, and non-toxic.

Without wishing to be limited by theory, modified cellulose (e.g., CMC and/or sodium CMC) can form hydrogen bonds with nonwoven fibers (e.g., cellulosic fiber), as well as covalent bonds, such as ester type bonds, thereby increasing the strength of nonwovens.

Nonlimiting examples of commercially available CMC and sodium CMC suitable for use in the present disclosure include AQUALON sodium CMC available from Ashland; GELYCEL sodium CMC available from Amtex; WALOCEL CMC available from Dow; and the like; or combinations thereof.

In an aspect, the cellulosic binder can comprise the modified cellulose in an amount of from about 50 wt. % to about 99 wt. %, alternatively from about 55 wt. % to about 94 wt. %, or alternatively from about 60 wt. % to about 89 wt. %.

In an aspect, a cellulosic binder can comprise modified cellulose and a crosslinking agent in a weight ratio of crosslinking agent to modified cellulose of from about 1:2 to about 1:1,000, alternatively from about 1:3 to about 1:750, alternatively from about 1:4 to about 1:500, or alternatively from about 1:5 to about 1:100.

In an aspect, the cellulosic binder can comprise a crosslinking agent, wherein the crosslinking agent comprises a carboxylic acid having two or more carboxyl groups. Nonlimiting examples of carboxylic acids having two or more carboxyl groups suitable for use as crosslinking agent in the present disclosure include citric acid, oxalic acid, malonic acid, succinic acid, glutaric acid, adipic acid, malic acid, polyacrylic acid, and the like, or combinations thereof. In an aspect, the crosslinking agent comprises citric acid. As will be appreciated by one of skill in the art, and with the help of this disclosure, the crosslinking agents disclosed herein can be used in foods, cosmetics, and even in pharmaceutics, owing to being biocompatible, biodegradable, and non-toxic.

Without wishing to be limited by theory, the crosslinking agent of the type disclosed herein comprises carboxyl groups which can form covalent bonds (e.g., ester type bonds), as well as hydrogen bonds, with both nonwoven fibers (e.g., cellulosic fibers), and with the modified cellulose, thereby providing nonwovens with increased wet strength and/or increased dry strength.

In an aspect, the cellulosic binder can comprise the crosslinking agent in an amount of from about 1 wt. % to about 50 wt. %, alternatively from about 6 wt. % to about 45 wt. %, or alternatively from about 11 wt. % to about 40 wt. %.

In some aspects, the cellulosic binder can comprise modified cellulose and crosslinking agent in a weight ratio of crosslinking agent to modified cellulose of about 1:2.5.

In an aspect, a cellulosic binder can comprise modified cellulose and a wet strength agent. For purposes of the disclosure herein, the term "wet strength agent" refers to a compound that can improve the strength (e.g., tensile strength; wet tensile strength) properties of nonwoven materials. Generally, a wet strength agent can be used in nonwovens to improve strength properties of nonwoven materials. In an aspect, the wet strength agent can comprise at least one reactive functional group selected from the group consisting of a halide group, a chloride group, a fluoride group, a hydroxyl group, and combinations thereof. Without wishing to be limited by theory, a wet strength agent of the type disclosed herein can form chemical bonds (e.g., covalent bonds, ionic bonds) with the modified cellulose and/or nonwoven fibers, for example via the at least one reactive functional group, thereby improving the strength of nonwovens. For purposes of the disclosure herein, the term "reactive functional group" refers to a functional group that can undergo a reaction to form chemical bonds (e.g., covalent bonds, ionic bonds) with the modified cellulose and/or nonwoven fibers, for example under the conditions of treating the fiber web with the cellulosic binder, curing the binder, etc.

In some aspects, a cellulosic binder can comprise modified cellulose and a wet strength agent in a weight ratio of wet strength agent to modified cellulose of from about 1:2 to about 1:1,000, alternatively from about 1:3 to about 1:750, alternatively from about 1:4 to about 1:500, or alternatively from about 1:5 to about 1:100; wherein the wet strength agent can comprise at least one reactive functional group selected from the group consisting of a halide group, a chloride group, a fluoride group, a hydroxyl group, and combinations thereof.

In an aspect, the cellulosic binder can comprise a wet strength agent in an amount of from about 1 wt. % to about 50 wt. %, alternatively from about 6 wt. % to about 45 wt. %, or alternatively from about 11 wt. % to about 40 wt. %.

Nonlimiting examples of a wet strength agent suitable for use in the present disclosure include N-methylolacrylamide (NMA), polyacrylamide (PAM), glyoxylated polyacrylamide (GPAM), polyamide epichlorohydrin (PAE) (e.g., POLYCUP crosslinking resins, such as POLYCUP 2000), polyamidoamine epichlorohydrin (PAAE), and the like, or combinations thereof.

Nonlimiting examples of commercially available wet strength agent suitable for use in the present disclosure include POLYCUP crosslinking resins, which are formaldehyde-free, water-based resins that are reactive with amine, carboxyl, hydroxyl and thiol functionality, and which are available from Solenis; FENNOBOND bonding agent available from Kemira; and the like; or combinations thereof.

In some aspects, the cellulosic binder as disclosed herein can comprise modified cellulose and a binder modifier, wherein the binder modifier comprises a crosslinking agent, a wet strength agent, or both a crosslinking agent and a wet strength agent.

In an aspect, the cellulosic binder as disclosed herein can comprise modified cellulose and a wet strength agent, wherein the wet strength agent comprises at least one reactive functional group selected from the group consisting of a halide group, a chloride group, a fluoride group, a hydroxyl group, and combinations thereof. In such aspect, the cellulosic binder can comprise modified cellulose and wet strength agent in a weight ratio of wet strength agent to modified cellulose of from about 1:2 to about 1:1,000, alternatively from about 1:3 to about 1:750, alternatively from about 1:4 to about 1:500, or alternatively from about 1:5 to about 1:100. In some aspects, the cellulosic binder can comprise modified cellulose and wet strength agent in a weight ratio of wet strength agent to modified cellulose of about 1:2.5.

In an aspect, the cellulosic binder can further comprise a softening agent in an amount of from about 1 wt. % to about 25 wt. %, alternatively from about 2 wt. % to about 20 wt. %, or alternatively from about 3 wt. % to about 10 wt. %. Generally, a softening agent can be used in nonwovens to provide specific softness, hydrophilicity, antistatic properties, etc. As will be appreciated by one of skill in the art, and with the help of this disclosure, softening agents can also reduce the water absorbency of nonwovens.

Nonlimiting examples of a softening agent suitable for use in the present disclosure include an anionic surfactant, glycerol, a polyethylene emulsion, ethylene glycol, polyethylene glycol, propylene glycol, polypropylene glycol, butylene glycol, a fatty alcohol ethoxylate, sodium lauryl sulfate, a silicone-based softener, a nanomaterials-based softener, and the like, or combinations thereof.

In an aspect, the cellulosic binder as disclosed herein can comprise modified cellulose, a binder modifier, and a softening agent. In some aspects, the cellulosic binder as disclosed herein can comprise modified cellulose, a crosslinking agent, and a softening agent. In other aspects, the cellulosic binder as disclosed herein can comprise modified cellulose, a wet strength agent, and a softening agent. In yet other aspects, the cellulosic binder as disclosed herein can comprise modified cellulose, a crosslinking agent, a wet strength agent, and a softening agent.

In an aspect, the cellulosic binder can comprise binder modifier and softening agent in a weight ratio of softening agent to binder modifier of from about 1:10 to about 2:1, alternatively from about 1:5 to about 1.5:1, or alternatively from about 1:2 to about 1:1. In some aspects, the cellulosic binder can comprise binder modifier and softening agent in a weight ratio of softening agent to binder modifier of about 1:1.

In some aspects, the cellulosic binder can comprise modified cellulose, binder modifier and softening agent in a weight ratio of modified cellulose to binder modifier to softening agent of about 2.5:1:1, wherein the binder modifier comprises a crosslinking agent, a wet strength agent, or both a crosslinking agent and a wet strength agent. In some aspects, the cellulosic binder can comprise modified cellulose, crosslinking agent and softening agent in a weight ratio of modified cellulose to crosslinking agent to softening agent of about 2.5:1:1. In other aspects, the cellulosic binder can comprise modified cellulose, wet strength agent and softening agent in a weight ratio of modified cellulose to wet strength agent to softening agent of about 2.5:1:1.

In some aspects, the cellulosic binder can comprise modified cellulose and an electrolyte. Generally, an electrolyte can decrease the viscosity of an aqueous solution of modified cellulose.

In an aspect, the cellulosic binder can further comprise an electrolyte in an amount of from about 0.01 wt. % to about 5 wt. %, alternatively from about 0.01 wt. % to about 2.5 wt. %, alternatively from about 0.01 wt. % to about 1 wt. %, alternatively from about 0.01 wt. % to about 0.5 wt. %, alternatively from about 0.02 wt. % to about 0.3 wt. %, or alternatively from about 0.05 wt. % to about 0.1 wt. %.

Nonlimiting examples of an electrolyte suitable for use in the present disclosure include NaCl, KCl, $CaCl_2$, $MgCl_2$, $AlCl_3$, $Na_2SO_4$, $Al_2SO_4$, $K_2SO_4$, $CaSO_4$, alum $(KAl(SO_4)_2 \cdot 12H_2O)$, and the like, or combinations thereof.

In an aspect, the cellulosic binder can comprise water (e.g., aqueous cellulosic binder).

In some aspects, the aqueous cellulosic binder comprises modified cellulose and water.

In other aspects, the aqueous cellulosic binder comprises modified cellulose, water, and an electrolyte.

In yet other aspects, the aqueous cellulosic binder comprises modified cellulose, water, and a binder modifier. For example, the aqueous cellulosic binder comprises modified cellulose, water, and a crosslinking agent. As another example, the aqueous cellulosic binder comprises modified cellulose, water, and a water strength agent. As yet another example, the aqueous cellulosic binder comprises modified cellulose, water, a crosslinking agent, and a water strength agent.

In an aspect, the aqueous cellulosic binder comprises modified cellulose, a crosslinking agent, and water. In an aspect, the aqueous cellulosic binder can be a sprayable aqueous solution. As will be appreciated by one of skill in the art, and with the help of this disclosure, if any of the components used for preparing the aqueous cellulosic binder contain water (e.g., modified cellulose solution, crosslinking agent aqueous solution), such water will be present in the aqueous cellulosic binder, and will contribute to the total amount of water in the final aqueous cellulosic binder composition.

In an aspect, the aqueous cellulosic binder can be characterized by a weight ratio of water to modified cellulose of from about 99.9:0.1 to about 1,000:500 (i.e., from about 999:1 to about 2:1), alternatively from about 99:1 to about 500:100 (i.e., from about 99:1 to about 5:1), or alternatively from about 50:1 to about 100:10 (i.e., from about 50:1 to about 10:1).

In an aspect, the aqueous cellulosic binder can be characterized by a weight ratio of crosslinking agent to modified cellulose of from about 1:2 to about 1:1,000, alternatively from about 1:3 to about 1:750, alternatively from about 1:4 to about 1:500, or alternatively from about 1:5 to about 1:100.

In an aspect, the aqueous cellulosic binder can comprise the modified cellulose in an amount of from about 0.1 wt. % to about 50 wt. %, alternatively from about 1 wt. % to about 40 wt. %, or alternatively from about 2.5 wt. % to about 25 wt. %.

In an aspect, the aqueous cellulosic binder can comprise the crosslinking agent in an amount of from about 0.1 wt. % to about 10 wt. %, alternatively from about 0.5 wt. % to about 5 wt. %, or alternatively from about 1 wt. % to about 2.5 wt. %.

In an aspect, the aqueous cellulosic binder can have a pH of from about 2 to about 8, alternatively from about 3 to about 6, or alternatively from about 4 to about 5.

In an aspect, the aqueous cellulosic binder can comprise a wet strength agent in an amount of from about 0.1 wt. % to about 10 wt. %, alternatively from about 0.5 wt. % to about 5 wt. %, or alternatively from about 1 wt. % to about 2.5 wt. %; wherein the wet strength agent comprises at least one reactive functional group selected from the group consisting of a halide group, a chloride group, a fluoride group, a hydroxyl group, and combinations thereof.

In some aspects, the aqueous cellulosic binder as disclosed herein can comprise a binder modifier in an amount of from about 0.1 wt. % to about 10 wt. %, alternatively from about 0.5 wt. % to about 5 wt. %, or alternatively from about 1 wt. % to about 2.5 wt. %; wherein the binder modifier comprises a crosslinking agent, a wet strength agent, or both a crosslinking agent and a wet strength agent.

In an aspect, the aqueous cellulosic binder as disclosed herein can further comprise a softening agent in an amount of from about 0.1 wt. % to about 10 wt. %, alternatively from about 0.5 wt. % to about 5 wt. %, or alternatively from about 1 wt. % to about 2.5 wt. %.

In an aspect, the aqueous cellulosic binder as disclosed herein can further comprise an electrolyte in an amount of from about 0.1 wt. % to about 10 wt. %, alternatively from about 0.1 wt. % to about 5 wt. %, alternatively from about 0.1 wt. % to about 4 wt. %, alternatively from about 0.1 wt. % to about 3 wt. %, alternatively from about 0.1 wt. % to about 2 wt. %, alternatively from about 0.1 wt. % to about 1 wt. %, alternatively from about 0.2 wt. % to about 0.9 wt. %, or alternatively from about 0.3 wt. % to about 0.8 wt. %.

In an aspect, the cellulosic binder and/or aqueous cellulosic binder as disclosed herein can be biodegradable. Generally, the term "biodegradable" refers to a material that is capable of degrading or decaying through the action of living organisms, such as bacteria and fungi.

In some aspects, the cellulosic binder and/or aqueous cellulosic binder can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In an aspect, the cellulosic binder and/or aqueous cellulosic binder can be characterized by a degree of biodegradability of 100%, wherein the degree of biodegradability refers to aerobic biodegradability in soil as determined in accordance with ISO 17556:2003 E.

In an aspect, the aqueous cellulosic binder can be made by using any suitable methodology.

In an aspect, a method of making an aqueous cellulosic binder can generally comprise contacting modified cellulose with water, and optionally an electrolyte to form a modified cellulose solution; wherein the modified cellulose comprises CMC and/or sodium CMC. In some aspects, the modified cellulose solution can be used as the aqueous cellulosic binder. In aspects where the modified cellulose solution is used as an aqueous binder solution (e.g., aqueous cellulosic binder), the modified cellulose solution can be referred to as "aqueous cellulosic binder," and the terms "aqueous cellulosic binder" and "modified cellulose solution" can be used interchangeably for purposes of the disclosure herein.

In some aspects, the modified cellulose solution (e.g., aqueous cellulosic binder) can be used in a process for making a nonwoven fabric as disclosed herein, for example by contacting a fiber web with the modified cellulose solution (e.g., aqueous cellulosic binder), as described in more detail later herein.

In some aspects, a method of making an aqueous cellulosic binder as disclosed herein can generally comprise the steps of (a) contacting modified cellulose with water to form a modified cellulose solution, wherein the modified cellulose comprises CMC and/or sodium CMC; and (b) contacting at least a portion of the modified cellulose solution with an electrolyte to form the aqueous cellulosic binder; wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, and wherein the aqueous cellulosic binder is characterized by a weight ratio of electrolyte to modified cellulose of from about 1:10 to about 1:1,000, alternatively from about 1:50 to about 1:500, or alternatively from about 1:100 to about 1:250.

In other aspects, the modified cellulose solution can be further contacted with a binder modifier to form the aqueous cellulosic binder, wherein the aqueous cellulosic binder can be used in a process for making a nonwoven fabric as disclosed herein, for example by contacting a fiber web with the aqueous cellulosic binder, as described in more detail later herein. The binder modifier can comprise a crosslinking agent and/or a wet strength agent, wherein the crosslinking agent comprises a carboxylic acid having two or more carboxyl groups, and wherein the wet strength agent comprises at least one reactive functional group selected from the group consisting of a halide group, a chloride group, a fluoride group, a hydroxyl group, and combinations thereof.

In an aspect, a method of making an aqueous cellulosic binder can comprise a step of contacting modified cellulose (e.g., CMC and/or sodium CMC) with water to form a modified cellulose solution. In an aspect, the step of contacting modified cellulose with water to form a modified cellulose solution can further comprise mixing, agitating, stirring, shaking, sonicating (e.g., ultrasonicating), and the like, or combinations thereof to facilitate the modified cellulose solubilizing in the solution. As will be appreciated by one of skill in the art, and with the help of this disclosure, the modified cellulose can be contacted with water under agitation, for example by magnetic stirring, to facilitate the modified cellulose solubilizing in the solution.

In an aspect, the modified cellulose solution can be prepared by combining the modified cellulose with water in any suitable order.

In some aspects, the modified cellulose can be added to water, wherein the resulting mixture can be further agitated, for example by magnetic stirring, to facilitate the modified cellulose solubilizing in the solution.

In other aspects, water can be added to the modified cellulose, for example water can be poured onto the modified cellulose, and the resulting mixture can be agitated, for example by magnetic stirring, to facilitate the modified cellulose solubilizing in the solution.

In an aspect, the modified cellulose solution can have a pH of from about 4 to about 8, alternatively from about 5 to about 7, or alternatively from about 6 to about 7.

In an aspect, the modified cellulose solution can comprise the modified cellulose in an amount of from about 0.1 wt. % to about 50 wt. %, alternatively from about 1 wt. % to about 40 wt. %, or alternatively from about 2.5 wt. % to about 25 wt. %.

In an aspect, a method of making an aqueous cellulosic binder can comprise a step of contacting at least a portion of the modified cellulose solution with a crosslinking agent to form the aqueous cellulosic binder. In an aspect, the step of contacting at least a portion of the modified cellulose solution with a crosslinking agent to form the aqueous cellulosic binder can further comprise mixing, agitating, stirring, shaking, sonicating, and the like, or combinations thereof to facilitate the crosslinking agent solubilizing in the solution. As will be appreciated by one of skill in the art, and with the help of this disclosure, the modified cellulose solution can be contacted with the crosslinking agent under agitation.

In an aspect, the aqueous cellulosic binder can be prepared by combining the modified cellulose solution with the crosslinking agent in any suitable order.

In some aspects, the modified cellulose solution can be added to the crosslinking agent (e.g., the modified cellulose solution can be poured onto the crosslinking agent), for example under agitation, such as by magnetic stirring, to facilitate the crosslinking agent solubilizing in the solution.

In other aspects, the crosslinking agent can be added to the modified cellulose solution, for example under agitation, such as by magnetic stirring, to facilitate the crosslinking agent solubilizing in the solution.

In some aspects, the crosslinking agent can be contacted with the modified cellulose solution in a solid state. In such aspects, the method of making an aqueous cellulosic binder can advantageously eliminate a step of solubilizing the crosslinking agent prior to contacting the crosslinking agent with the modified cellulose solution.

In other aspects, the crosslinking agent can be first solubilized in water to form a crosslinking agent aqueous solution, wherein the modified cellulose solution can be contacted with the crosslinking agent aqueous solution to form the aqueous cellulosic binder. As will be appreciated by one of skill in the art, and with the help of this disclosure, when the crosslinking agent is used in the form of a crosslinking agent aqueous solution for preparing the aqueous cellulosic binder, the water present in the crosslinking agent aqueous solution contributes to the total amount of water in the final aqueous cellulosic binder composition.

In yet other aspects, the modified cellulose in solid state can be contacted with the crosslinking agent aqueous solution in any suitable order to form the aqueous cellulosic binder.

In still yet other aspects, the modified cellulose in solid state can be contacted with (e.g., mixed with) the crosslinking agent in solid state, and the resulting solid mixture can be then solubilized in water to form the aqueous cellulosic binder.

In an aspect, a method of making an aqueous cellulosic binder can further comprise contacting the aqueous cellulosic binder with an additive selected from the group consisting of a softening agent, an electrolyte, a pigment color, and combinations thereof. In such aspect, contacting the aqueous cellulosic binder with an additive can further comprise mixing, agitating, stirring, shaking, sonicating, and the like, or combinations thereof.

In an aspect, a method of making an aqueous cellulosic binder can comprise a step of contacting at least a portion of the modified cellulose solution with a binder modifier to form the aqueous cellulosic binder, as previously disclosed herein for the crosslinking agent; wherein the binder modifier comprises a crosslinking agent, a wet strength agent, or both a crosslinking agent and a wet strength agent. In an aspect, the step of contacting at least a portion of the modified cellulose solution with a binder modifier to form the aqueous cellulosic binder can further comprise mixing, agitating, stirring, shaking, sonicating, and the like, or combinations thereof to facilitate the binder modifier solubilizing in the solution, as previously disclosed herein for the crosslinking agent. As will be appreciated by one of skill in the art, and with the help of this disclosure, the modified cellulose solution can be contacted with the binder modifier under agitation.

In an aspect, the aqueous cellulosic binder can be prepared by combining the modified cellulose solution with the binder modifier in any suitable order, as previously disclosed herein for the crosslinking agent.

In an aspect, a method of making an aqueous cellulosic binder can further comprise contacting the aqueous cellulosic binder with wet strength agent. In such aspect, contacting the aqueous cellulosic binder with a wet strength agent can further comprise mixing, agitating, stirring, shaking, sonicating, and the like, or combinations thereof.

In an aspect, a method of making an aqueous cellulosic binder can comprise a step of contacting at least a portion of the modified cellulose solution with a wet strength agent to form the aqueous cellulosic binder, as previously disclosed herein for the crosslinking agent. In an aspect, the step of contacting at least a portion of the modified cellulose solution with a wet strength agent to form the aqueous cellulosic binder can further comprise mixing, agitating, stirring, shaking, sonicating, and the like, or combinations thereof to facilitate the wet strength agent solubilizing in the solution, as previously disclosed herein for the crosslinking agent. As will be appreciated by one of skill in the art, and with the help of this disclosure, the modified cellulose solution can be contacted with the wet strength agent under agitation.

In an aspect, the aqueous cellulosic binder can be prepared by combining the modified cellulose solution with the wet strength agent in any suitable order, as previously disclosed herein for the crosslinking agent.

In an aspect, the cellulosic binder as disclosed herein can be used in a process for producing nonwovens. As used herein, a "nonwoven," a "nonwoven material," or a "nonwoven fabric" refers to a sheet of fibers, continuous filaments, or chopped yarns of any nature or origin, that have been formed into a web by any means, and bonded together by at least the cellulosic binder described herein, wherein weaving or knitting is not involved in forming and/or bonding the web. Further, for purposes of the disclosure herein, a "nonwoven," a "nonwoven material," or a "nonwoven fabric" refers to sheet or web structures made of fiber, filaments, molten plastic, or plastic films bonded together at least chemically (e.g., bonding with a cementing medium or binder, such as the cellulosic binder as disclosed herein), although other types of bonding can be used for producing nonwovens, such as thermal bonding (e.g., fusing of the fibers, as in the case of thermoplastic fibers), mechanical bonding (e.g., mechanical interlocking of fibers in a random web or mat), etc. Web bonding processes impart integrity to the web and the resulting material is often referred to as fabric(s). Often, the fabrics can undergo further mechanical and/or chemical finishing or both in order to achieve enhanced properties and appearance. As will be appreciated by one of skill in the art, and with the help of this disclosure, all these processes along with the choice of fibers determine the structures and properties of the nonwoven fabrics.

A variety of processes can be used to assemble the nonwoven fabrics described herein, including but not limited to, traditional wet laying processes and dry forming processes such as air-laying and carding, or any other suitable forming technologies such as spunlace or airlaid. In an aspect, the nonwoven fabrics can be prepared by an airlaid process. Processes and equipment suitable for the production of nonwoven materials are described in more detail U.S. Pat. Nos. 4,335,066; 4,732,552; 4,375,448; 4,366,111; 4,375,447; 4,640,810; 206,632; 2,543,870; 2,588,533; 5,234,550; 4,351,793; 4,264,289; 4,666,390; 4,582,666; 5,076,774; 874,418; 5,566,611; 6,284,145; 6,363,580; and 6,726,461; each of which is incorporated by reference herein in its entirety.

In an aspect, the nonwovens as disclosed herein can be made by using any suitable methodology. In an aspect, a method of making a nonwoven fabric can comprise a step of forming a plurality of fibers into a fiber web. Generally, a web forming process is a process that disperses the fibers or filaments to form a sheet or web and can also stack the webs to form multi-layered webs, which are sometimes referred to as batts.

In some aspects, the step of forming a plurality of fibers into a fiber web can be a wet laid process. In other aspects, the step of forming a plurality of fibers into a fiber web can be a dry laid process. In yet other aspects, the step of forming a plurality of fibers into a fiber web can be a spunlaid process.

Generally, techniques for wet laying fibrous material to form sheets, such as dry lap and paper, are well known in the art. Suitable wet laying techniques include, but are not limited to, hand sheeting and wet laying with paper making machines as disclosed in U.S. Pat. No. 3,301,746, which is incorporated by reference herein in its entirety. The principle of wet laying is similar to paper manufacturing. The difference lies in the amount of synthetic fibers present in a wet laid nonwoven material. A dilute slurry of water and fibers can be deposited on a moving wire screen and drained to form a web. The web can be further dewatered, consolidated, by pressing between rollers, and dried. Impregnation with binders (e.g., cellulosic binder) can follow the web forming process. The strength of a randomly oriented web is rather similar in all directions in the plane of the fabric for wet laid nonwovens.

The dry laid process can include a mechanical process known as carding, which is described in more detail in U.S. Pat. No. 797,749, which is incorporated by reference herein in its entirety. The carding process can include an airstream component to randomize the orientation of fibers when they are collected on a forming wire. Typically, the fiber length for a mechanically carded process can be in the range of 38-60 mm. Longer fiber lengths can be possible depending on the set up of the card. Some mechanical cards, such as the Truzschler-Fliessner EWK-413 card, can run fibers having significantly shorter length than 38 mm.

In an aspect, the dry laid process can comprise an airlaid process (e.g., air-forming process). The airlaid process employs only air flow, gravity, and centripetal force to deposit a stream of fibers onto a moving forming wire that conveys the fiber web to a web bonding process (e.g., chemical bonding with a cellulosic binder). The airlaid process is effective at forming a uniform web of short fibers, e.g., typically less than 6 mm long, with low fiber to fiber cohesion and low potential for generating static. The dominant fiber utilized in these air driven processes is wood pulp, which can be processed at high throughput owing to its short length of 3 mm or less. Typically, fiber lengths above 12 mm are commercially impractical for airlaid processes. Pulp-based air-formed nonwoven webs frequently incorporate 10% to 20% of 4 to 6 mm thermoplastic fibers that could melt and additionally bond the airlaid web together when the air-formed web is heated, for example by passing through ovens. Without wishing to be limited by theory, it is possible to air-form a layer of 100% thermoplastic fiber; however, the fiber throughput rate typically declines significantly with increasing fiber length. Airlaid processes are described in more detail in U.S. Pat. Nos. 4,014,635 and 4,640,810; each of which is incorporated by reference herein in its entirety.

Generally, spunlaid (also known as spunbond or spun-bonded) and meltblown processes are types of spunmelt processes, where "spunmelt" is a generic term describing the manufacturing of nonwoven fiber webs directly from thermoplastic polymers. During spunlaid processes, polymer granules can be melted, and molten polymer can be extruded through spinnerets, resulting in continuous polymeric filaments that are then cooled and deposited onto a conveyor to form a fiber web. While the temperature of the polymeric filaments can cause them to adhere to one another on the conveyor, such bonding is generally insufficient, and the spunlaid fiber webs require further bonding, for example by using a cellulosic binder as disclosed herein.

In an aspect, the plurality of fibers can comprise natural fibers (e.g., cellulosic or cellulose fibers), synthetic fibers, or both. Any cellulosic fibers known in the art, including cellulose fibers of any natural origin, such as those derived from wood pulp, may be used for forming the web. Nonlimiting examples of natural fibers suitable for use in the present disclosure for forming the web include, but are not limited to, wood cellulose; cotton linter pulp; chemically modified cellulose, such as crosslinked cellulose fibers; highly purified cellulose fiber; digested fibers, such as kraft digested fibers, prehydrolyzed kraft digested fibers, soda digested fibers, sulfite digested fibers; chemi-thermally treated fibers, mechanically treated fibers, thermo-mechanically treated fibers; fibers derived from softwoods, such as pines, firs, and spruces; fibers derived from hardwood, such as eucalyptus; fibers derived from Esparto grass, bagasse, kemp, flax, hemp, kenaf, and other lignaceous and cellulosic fiber sources; and the like; or combinations thereof. Non-limiting examples of natural fibers suitable for use in the present disclosure for forming the web include FOLEY FLUFFS fibers, which are bleached Kraft southern pine fibers available from Georgia-Pacific; cellulose pulp fibers, which are a southern softwood fluff pulp available from Georgia-Pacific; HPF, which is a highly purified cellulose fiber available from Georgia-Pacific; and T 730 hardwood pulp, which is an eucalyptus pulp available from Weyerhaeuser.

In an aspect, the plurality of fibers can comprise synthetic fibers. Nonlimiting example of synthetic fibers suitable for use in the present disclosure for forming the web include acrylic polymers, polyamides (e.g., Nylon 6, Nylon 6/6, Nylon 12, polyaspartic acid, polyglutamic acid, etc.), polyamines, polyimides, polyacrylics (e.g., polyacrylamide, polyacrylonitrile, esters of methacrylic acid and acrylic acid, etc.), polycarbonates (e.g., polybisphenol A carbonate, polypropylene carbonate, etc.), polydienes (e.g., polybutadiene, polyisoprene, polynorbornene, etc.), polyepoxides, polyesters (e.g., polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, polypropylene succinate, etc.), polyethers (e.g., polyethylene glycol (polyethylene oxide), polybutylene glycol, polypropylene oxide, polyoxymethylene (paraformaldehyde), polytetramethylene ether (polytetrahydrofuran), polyepichlorohydrin, etc.), polyfluorocarbons, formaldehyde polymers (e.g., urea-formaldehyde, melamine-formaldehyde, phenol formaldehyde), natural polymers (e.g., cellulosics, chitosans, lignins, waxes, etc.), polyolefins (e.g., polyethylene, polypropylene, polybutylene, polybutene, polyoctene, etc.), polyphenylenes (e.g., polyphenylene oxide, polyphenylene sulfide, polyphenylene ether sulfone, etc.), silicon containing polymers (e.g., polydimethyl siloxane, polycarbomethyl silane, etc.), polyurethanes, polyvinyls (e.g., polyvinyl butyral, polyvinyl alcohol, esters and ethers of polyvinyl alcohol, polyvinyl acetate, polystyrene, polymethylstyrene, polyvinyl chloride, polyvinyl pryrrolidone, polymethyl vinyl ether, polyethyl vinyl ether, polyvinyl methyl ketone, etc.), polyacetals, polyarylates, and copolymers (e.g., polyethylene-co-vinyl acetate, polyethylene-co-acrylic acid, polybutylene terephthalate-co-polyethylene terephthalate, polylauryllactam-block-polytetrahydrofuran, etc.), polylactic acid (PLA) based polymers, polybutylene succinate (PBS) based polymers, derivatives thereof, copolymers thereof, and the like, or combinations thereof.

In some aspects, the fiber web can comprise natural fibers (which are biodegradable) and biodegradable synthetic fibers, such as PLA-based polymeric fibers and/or PBS-based polymeric fibers. In an aspect, the biodegradable synthetic fibers (e.g., PLA-based polymeric fibers and/or PBS-based polymeric fibers) can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In such aspects, the biodegradable synthetic fibers (e.g., PLA-based polymeric fibers and/or PBS-based polymeric fibers) can be characterized by a degree of biodegradability of 100%, wherein the degree of biodegradability refers to aerobic biodegradability in soil as determined in accordance with ISO 17556:2003 E. In aspects where the fiber web comprises natural fibers and biodegradable synthetic fibers (e.g., PLA-based polymeric fibers and/or PBS-based polymeric fibers), the nonwoven fabric and the fiber web can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In such aspects, the nonwoven fabric and the fiber web can be characterized by a degree of biodegradability of 100%, wherein the degree of biodegradability refers to aerobic biodegradability in soil as determined in accordance with ISO 17556:2003 E.

In aspects where the fiber web comprises natural fibers and non-biodegradable synthetic fibers, the nonwoven fabric can be non-biodegradable. In such aspects, the non-biodegradable synthetic fibers can comprise polyethylene terephthalate (PET) and/or polyethylene (PE). For example, non-biodegradable synthetic fibers can comprise bicomponent fibers comprising PET and/or PE as disclosed herein. Generally, the term "non-biodegradable" refers to a material that is not capable of degrading or decaying through the action of living organisms, such as bacteria and fungi.

In an aspect, the synthetic fibers can comprise monocomponent fibers (i.e., single synthetic polymer or copolymer component in the fibers), bicomponent fibers (i.e., two synthetic polymer or copolymer components in the fibers), multicomponent fibers (i.e., more than two synthetic polymer or copolymer components in the fibers), or combinations thereof.

In some aspects, the synthetic fibers can comprise monocomponent fibers, wherein the monocomponent fibers can comprise polyethylene, polypropylene, polyester, polylactic acid (PLA), and the like, or combinations thereof.

In some aspects, the synthetic fibers can comprise multicomponent fibers, for example multicomponent fibers having enhanced reversible thermal properties. Generally, multicomponent fibers contain temperature regulating materials, such as phase change materials having the ability to absorb or release thermal energy to reduce or eliminate heat flow. In general, a phase change material can comprise any substance, or mixture of substances, that has the capability of absorbing or releasing thermal energy to reduce or eliminate heat flow at or within a temperature stabilizing range. The temperature stabilizing range may comprise a particular transition temperature or range of transition temperatures. A phase change material used in nonwoven fabrics as disclosed herein can inhibit a flow of thermal energy during a time when the phase change material is absorbing or releasing heat, typically as the phase change material undergoes a transition between two states, such as, for example, liquid and solid states, liquid and gaseous states, solid and gaseous states, or two solid states. Phase changing is typically transient, and will occur until a latent heat of the phase change material is absorbed or released during a heating or cooling process. Thermal energy may be stored or removed from the phase change material, and the phase change material typically can be effectively recharged by a source of heat or cold. By selecting an appropriate phase change material, the multi-component fiber may be designed for use in any one of numerous products. Multicomponent fibers having enhanced reversible thermal properties are described in more detail in U.S. Pat. No. 6,855,422, which is incorporated by reference herein in its entirety.

In some aspects, the synthetic fibers can comprise bicomponent fibers. Generally, bicomponent fibers can have a core and a sheath surrounding the core, wherein the core and the sheath comprise different polymers. For example, the core comprises a first polymer, and the sheath comprises a second polymer, wherein the first polymer and the second polymer are different (e.g., the first polymer and the second polymer have different melting temperatures). Bicomponent fibers are typically used for producing nonwoven materials by airlaid techniques.

Bicomponent fibers may incorporate a variety of polymers as their core and sheath components. Bicomponent fibers that have a polyethylene (PE) or modified PE sheath typically have a polyethyleneterephthalate (PET) or polypropylene (PP) core. In an aspect, the bicomponent fiber can have a core made of polyester and a sheath made of polyethylene.

In an aspect, bicomponent fibers can have a length of equal to or greater than about 6 mm, alternatively equal to or greater than about 8 mm, alternatively equal to or greater than about 10 mm, alternatively equal to or greater than about 12 mm, alternatively from about 3 mm to about 36 mm, alternatively from about 4 mm to about 24 mm, alternatively from about 5 mm to about 18 mm, or alternatively from about 6 mm to about 12 mm. The bicomponent fibers suitable for use in the present disclosure can have any suitable geometry, such as concentric, eccentric, side by side, islands in a sea, pie segments and other variations.

Various degrees of stretching, drawing or draw ratios can be used for the bicomponent fibers suitable for use in the present disclosure, including partially drawn and highly drawn bicomponent fibers and homopolymers. These fibers can include a variety of polymers and may have a partially drawn core, a partially drawn sheath or a partially drawn core and sheath, or they may be a homopolymer that is partially drawn. In some aspects, the bicomponent fibers can have a partially drawn core. Highly drawn bicomponent fibers are described in more detail later herein.

The bicomponent fibers suitable for use in the present disclosure can include fibers that utilize a partially drawn polyester core with a variety of sheath materials, specifically including a polyethylene sheath. The use of both partially drawn and highly drawn bicomponent fibers in the same structure can be leveraged to meet specific physical and performance properties based on how the fibers are incorporated into the structure. The degree to which the partially drawn bicomponent fibers are drawn is not limited in scope as different degrees of drawing will yield different enhancements in performance. The scope of the partially drawn bicomponent fibers encompasses fibers with various core sheath configurations including, but not limited to concentric, eccentric, side by side, islands in a sea, pie segments and other variations. In addition, the bicomponent fibers can comprise partially drawn homopolymers such as polyester, polypropylene, nylon, and other melt spinnable polymers. A nonlimiting example of partially drawn core bicomponent fibers suitable for use in the present disclosure include TREVIRA T265 bicomponent fibers, which are partially drawn core with a core made of polybutylene terephthalate (PBT) and a sheath made of polyethylene, and which are available from Trevira, Bobingen, Germany.

As used herein, the term "partially drawn core" or "partially drawn fiber" refers to all or part of a fiber, such as with a bicomponent fiber, that has not been drawn or stretched to achieve the highest possible tenacity or strength in its fiber form, but that some degree of drawing or stretching has been done to induce some degree of orientation or crystallinity and strength into the fiber. As such, a partially drawn core bicomponent fiber or a partially drawn homopolymer can still be capable of being stretched or drawn further once incorporated into an article. This allows the partially drawn core bicomponent fiber or partially drawn homopolymer to provide additional strength and elongation to the article as it is further drawn while incorporated within an article. A homopolymer or bicomponent fiber can be typically stretched close to the point of failure as this induces a high level of crystallinity and strength into the fiber form. The drawing or stretching of a filament, before it is cut into fibers, can occur in both the spinning and drawing steps. Drawing during the spinning step, also known as "drawdown," occurs when the molten fiber is pulled from the face of a spinneret resulting in drawing of the spun filament. Some degree of drawing is required in order to prevent the as-spun filament from becoming embrittled due to aging, which can cause a catastrophic failure, such as breaking, during the drawing step. Spinning and drawing homopolymer and bicomponent fibers are disclosed in more detail in U.S. Pat. Nos. 4,115,989; 4,217,321; 4,529,368; 4,687,610; 5,185,199; 5,372,885; and 6,841,245; each of which is incorporated by reference herein in its entirety. Some fibers, yarns and other melt spun or extruded materials can be referred to as undrawn, but still have some drawing during the melt spinning phase where the polymer is pulled away from the face of the spinneret. Some other fibers, yarns and other melt spun or extruded materials where no tension is applied to the fibers as they leave the face of the spinneret, for example adhesive polymers, can also be referred to as undrawn. Undrawn polymeric fibers suitable for use in the present disclosure are disclosed in more detail in U.S. Pat. Nos. 3,931,386, 4,021,410, 4,237,187, 4,434,204, 4,609,710, 5,229,060, 5,336,709, 5,634,249, 5,660,804, 5,773,825, 5,811,186, 5,849,232, 5,972,463, and 6,080,482, each of which is incorporated by reference herein in its entirety.

In an aspect, the bicomponent fibers can comprise highly drawn bicomponent fibers. As used herein, "highly drawn" is defined as being drawn or stretched close to the maximum level of drawing or stretching such that it will induce a high degree of molecular orientation in the fiber, and enhanced strength in the fiber form, without overdrawing or overstretching such that the fiber has a catastrophic failure and potentially breaks. In an aspect, the bicomponent fibers can comprise bicomponent fibers that are partially drawn with varying degrees of draw or stretch; highly drawn bicomponent fibers; and mixtures thereof. Nonlimiting examples of highly drawn bicomponent fibers suitable for use in the present disclosure include INVISTA T255 bicomponent fibers and TREVIRA T255 bicomponent fibers, which are highly drawn polyester core bicomponent fibers with a variety of sheath materials, specifically including a polyethylene sheath, and which are available from Invista, Salisbury, NC, and Trevira, Bobingen, Germany, respectively; and AL-Adhesion-C bicomponent fibers, which are highly drawn polypropylene core bicomponent fiber with a variety of sheath materials, specifically including a polyethylene sheath, which are available from ES FiberVisions, Varde, Denmark.

Bicomponent fibers suitable for use in the present disclosure are described in more detail in U.S. Pat. Nos. 5,372,885 and 5,456,982, each of which is incorporated by reference herein in its entirety. Processes for producing bicomponent fibers are described in more detail in U.S. Pat. Nos. 4,950,541, 5,082,899, 5,126,199, 5,372,885, 5,456,982, 5,705,565, 2,861,319, 2,931,091, 2,989,798, 3,038,235, 3,081,490, 3,117,362, 3,121,254, 3,188,689, 3,237,245, 3,249,669, 3,457,342, 3,466,703, 3,469,279, 3,500,498, 3,585,685, 3,163,170, 3,692,423, 3,716,317, 3,778,208, 3,787,162, 3,814,561, 3,963,406, 3,992,499, 4,052,146, 4,251,200, 4,350,006, 4,370,114, 4,406,850, 4,445,833, 4,717,325, 4,743,189, 5,162,074, 5,256,050, 5,505,889, 5,582,913, and 6,670,035, each of which is incorporated by reference herein in its entirety.

In an aspect, a method of making a nonwoven fabric can comprise a step of contacting at least a portion of the fiber web with the aqueous cellulosic binder to form a binder impregnated fiber web. The fiber web can be contacted with the aqueous cellulosic binder by using any suitable methodology. In an aspect, the aqueous cellulosic binder can be contacted with (e.g., applied to) the fiber web via a saturation bonding method, a foam bonding method, a spray bonding method, a print bonding method, and the like, or combinations thereof. The aqueous cellulosic binder can be any suitable aqueous cellulosic binder as disclosed herein. In some aspects, the aqueous cellulosic binder comprises modified cellulose, water, and optionally an electrolyte. In other aspects, the aqueous cellulosic binder comprises modified cellulose, water, and a binder modifier, wherein the binder modifier comprises a crosslinking agent and/or a wet strength agent.

In an aspect, the aqueous cellulosic binder can be used on one or both of the outer surfaces of the fiber web to control dusting, as will be discussed in more detail later herein, in addition to strengthening the fiber web. In aspects where it is desirable that the aqueous cellulosic binder be applied only on the outer surface of the substrate (e.g., fiber web), the aqueous cellulosic binder can be lightly sprayed, printed, foamed, or rolled onto the fiber web.

In an aspect, the step of contacting the fiber web with the aqueous cellulosic binder can comprise a saturation bonding process. Saturation chemical bonding involves complete immersion of a nonwoven web (e.g., fiber web) in a bath containing a binder (e.g., aqueous cellulosic binder), followed by the excess binder being removed by a pair of nip rolls (e.g., pinch rolls). The fiber web is guided through a saturation bath by rollers and then is pressed between a pair of nip rolls to squeeze out excess liquid (e.g., aqueous cellulosic binder). The amount of aqueous cellulosic binder taken up by the nonwoven depends on a variety of factors such as the basis weight of the nonwoven, length of time spent in the bath, wettability of the fibers, and nip pressure. The saturation bonding process can provide relatively high binder to fiber levels uniformly throughout the nonwoven. However, the saturation bonding process includes short wetting time, and as such is more suitable for lightweight and highly permeable nonwovens.

In an aspect, the step of contacting the fiber web with the aqueous cellulosic binder can comprise a foam bonding process, wherein air or water is used to dilute the aqueous cellulosic binder and as a mean to carry the binder to the fibers. Diluting the binder with air rather than with water has the advantage that drying is faster and energy cost is reduced remarkably. Binder foam can be generated mechanically and can be stabilized with a stabilizing agent to prevent collapse during application to the fiber web. Foam can be applied so as to remain at the surface of the fiber web or can be made to penetrate all the way through a fiber web cross-section. At least one reciprocating foam spreader is commonly used to distribute the foam across the width of the web/fabric. The excess foam can be removed through the porous portion of the web (e.g., space between fibers), for example via a vacuum extractor located on a side of the fiber web that is opposite to the side of the web where the foam is applied. Generally, foam bonding has more efficiency drying and the ability to control fabric softness. However, adequate foaming and uniform binder distribution can be difficult to achieve.

In an aspect, the step of contacting the fiber web with the aqueous cellulosic binder can comprise a print bonding process. Generally, for print bonding, the fiber web must be dry. The print bonding process applies the aqueous cellulosic binder only in predetermined areas as dictated by the pattern of the printing surfaces. The aqueous cellulosic binder can be transferred to the fiber web via a feed roll and an engraved roll. As the fiber web passes the engraved roll, it is pressed against the surface by a rubber roll, thereby transferring the aqueous cellulosic binder to the fabric in the predetermined areas. The excess of aqueous cellulosic binder can be removed by a doctor blade. The print bonding process is suitable for applying low levels of binder to the surface of the fiber web.

In an aspect, the step of contacting the fiber web with the aqueous cellulosic binder can comprise a spray bonding process, wherein the aqueous cellulosic binder can be sprayed onto the fiber web. The aqueous cellulosic binder can be sprayed onto a moving fiber web in fine droplet form through a system of nozzles. The spray bonding process can be used to make highly porous and bulky products, where the fiber web does not need to pass between nip rollers. Spraying the binder can provide an opportunity for the aqueous cellulosic binder solution to penetrate fibers material beneath the immediate surface of the fiber web being sprayed. The liquid binder (e.g., aqueous cellulosic binder) can be atomized by air pressure, hydraulic pressure, and/or centrifugal force and is generally applied to an upper surface of the fiber web. The depth of penetration of the binder into the substrate depends on a variety of factors such as the wettability of the fibers, permeability of the web, and amount of binder. The spray bonding process can allow for the nonwoven to not be compressed, thereby allowing the nonwoven to substantially retain original bulk and structure. In some aspects, the aqueous cellulosic binder can be sprayed onto a dry fiber web. In other aspects, the aqueous cellulosic binder can be sprayed onto a wet fiber web, such as a pre-wetted web.

In an aspect, the fiber web and the aqueous cellulosic binder can be contacted at a fabric to liquor ratio of from about 1:0.01 to about 1:20, alternatively from about 1:0.02 to about 1:18, alternatively from about 1:0.05 to about 1:15, or alternatively from about 1:0.07 to about 1:10, wherein the fabric to liquor ratio is a mass to volume ratio expressed in kg fiber web to liters of aqueous cellulosic binder. For example, a fabric to liquor ratio of 1:0.01 refers to a ratio of 1 kg of fiber web to 0.01 liters of aqueous cellulosic binder; a fabric to liquor ratio of 1:20 refers to a ratio of 1 kg of fiber web to 20 liters of aqueous cellulosic; etc. For purposes of the disclosure herein the term "liquor" refers to the aqueous cellulosic binder. Further, for purposes of the disclosure herein the term "fabric to liquor ratio" refers to the fabric to aqueous cellulosic binder ratio expressed in kg fiber web to liters of aqueous cellulosic binder.

In an aspect, a method of making a nonwoven fabric can comprise a step of curing the binder impregnated fiber web to form the nonwoven fabric, wherein the nonwoven fabric comprises a cured cellulosic binder, and wherein the cured cellulosic binder comprises at least a portion of the modified cellulose of the aqueous cellulosic binder and at least a portion of the crosslinking agent of the aqueous cellulosic binder.

In some aspects, a method of making a nonwoven fabric can comprise a step of curing the binder impregnated fiber web to form the nonwoven fabric, wherein the nonwoven fabric comprises a cured cellulosic binder, and wherein the cured cellulosic binder comprises at least a portion of the modified cellulose of the aqueous cellulosic binder and at least a portion of the binder modifier of the aqueous cellulosic binder; wherein the binder modifier comprises a crosslinking agent, a wet strength agent, or both a crosslinking agent and a wet strength agent.

As used herein, "curing," "cured" and similar terms are intended to encompass the structural and/or morphological change which occurs in a binder composition (e.g., aqueous binder composition) of the present disclosure, such as by covalent chemical reaction (crosslinking), ionic interaction or clustering, improved adhesion to the fiber web substrate, phase transformation or inversion, and hydrogen bonding when the binder composition is dried and heated to cure the binder. As used herein, the term "cured binder" refers to the cured product of the cellulosic binder, which cured product bonds the fibers of a fibrous product (e.g., fiber web) together. Generally, the bonding occurs at an intersection of overlapping fibers.

In an aspect, the step of curing the binder impregnated fiber web to form the nonwoven fabric can comprise drying the binder impregnated fiber web, for example by heating the binder impregnated fiber web to a temperature of from about 110° C. to about 220° C., alternatively from about 115° C. to about 215° C., alternatively from about 120° C. to about 210° C., alternatively from about 130° C. to about 200° C., or alternatively from about 140° C. to about 170° C. The binder impregnated fiber web can be heated by any suitable methodology.

After the binder is applied, the binder impregnated fiber web can be dried, for example in any suitable dryer or oven, to evaporate the binder carrier (e.g., water) and allow the cellulosic binder to bond the nonwovens, for example via chemical bonding (e.g., covalent bonding via the crosslinking agent, as previously described herein). Nonlimiting examples of dryers suitable for use in the present disclosure include drum dryers, heated drums, steam-heated drying cans, flat belt dryers, stenter-based dryers, thru-air ovens, perforated-drum dryers, infrared dryers, and the like, or combinations thereof. In drum drying or belt drying, the fiber web can be guided over a perforated conveyor surface through which hot air passes, for example air heated to a temperature of from about 110° C. to about 220° C. Air can then be withdrawn from the inside of the drum or through the perforations of the belt and can be reused. Stenter dryers can provide hot air flow to both surfaces of the binder impregnated fiber web. In infrared dryers, water from the binder absorbs infrared energy and it evaporates.

In an aspect, the step of curing the binder impregnated fiber web to form the nonwoven fabric can further comprise thermal bonding. As used herein, the term "thermal bonding" refers to a technique for bonding a web of fibers in which a heat and/or ultrasonic treatment, with or without pressure, is used to activate a heat-sensitive material. The heat-sensitive material can be in the form of fibers, bicomponent fibers and fusable powders, including as part of the web. The bonding may be applied all over (e.g., through bonding or area bonding) or restricted to predetermined, discrete sites (e.g., point bonding). Nonlimiting examples of thermal bonding suitable for use in the present disclosure include calendering, through-air thermal bonding, radiant heat bonding, sonic bonding, and the like, or combinations thereof. Calendering uses heat and high pressure applied through rollers to weld the fiber webs together. Through-air thermal bonding makes bulkier products by the overall bonding of a fiber web containing low melting point fibers, wherein the melting of the fibers takes place in a carefully temperature controlled hot air stream. Drum and blanket systems apply pressure and heat to make products of average bulk. Radiant heat bonding can be achieved by exposing the fiber web to a source of radiant energy in the infrared range, which increases the temperature of the web. Sonic bonding takes place when the molecules of the fibers held under a patterned roller are excited by high frequency energy which produces internal heating.

In an aspect, the fibers of the nonwoven material can be held together by the cellulosic binder; or by the cellulosic binder and melted or partially melted synthetic fibers, such as bicomponent fibers. In some aspects, the fiber web can comprise bicomponent fibers, wherein the bicomponent fibers comprise a core and a sheath surrounding the core. In such aspect, during thermal bonding of the binder impregnated fiber web at least a portion of the sheath can melt during the thermal bonding and can provide for further bonding of the fiber web.

In an aspect, a nonwoven fabric can comprise a fiber web as disclosed herein and a cured cellulosic binder as disclosed herein. The fiber web can be present in the nonwoven fabric in an amount of from about 85 wt. % to about 99.9 wt. %, alternatively from about 87 wt. % to about 99.5 wt. %, or alternatively from about 90 wt. % to about 99 wt. %, based on the total weight of the nonwoven fabric. The cured cellulosic binder can be present in the nonwoven fabric in an amount of from about 0.1 wt. % to about 15 wt. %, alternatively from about 0.5 wt. % to about 13 wt. %, or alternatively from about 1 wt. % to about 10 wt. %, based on the total weight of the nonwoven fabric. The nonwoven fabric can comprise natural fibers (e.g., cellulosic fibers) and/or synthetic fibers in any suitable amount to confer the desired properties to the nonwoven fabric.

In an aspect, the nonwoven fabric as disclosed herein can comprise a fiber web in an amount of from about 85 wt. % to about 99.9 wt. %, based on the total weight of the nonwoven fabric; and a cured cellulosic binder in an amount of from about 0.1 wt. % to about 15 wt. %, based on the total weight of the nonwoven fabric; wherein the cured cellulosic binder comprises modified cellulose, optionally an electrolyte, and optionally a binder modifier; wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, wherein the binder modifier comprises a crosslinking agent and/or a wet strength agent; wherein, when the binder modifier is present, the cured cellulosic binder is characterized by a weight ratio of binder modifier to modified cellulose of from about 1:2 to about 1:1,000; wherein the modified cellulose comprises CMC and/or sodium CMC; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

In an aspect, the fiber web can comprise cellulosic fibers in an amount of from about 50 wt. % to about 90 wt. %, alternatively from about 60 wt. % to 85 wt. %, or alternatively from about 70 wt. % to 80 wt. %, based on the total weight of the fiber web; and synthetic fibers (e.g., bicomponent fibers) in an amount of from 10 wt. % to about 50 wt. %, alternatively from about 15 wt. % to 40 wt. %, or alternatively from about 20 wt. % to about 30 wt. %, based on the total weight of the fiber web. In such aspect, the synthetic fibers can have a partially drawn core.

In an aspect, the nonwoven fabric as disclosed herein can include any suitable additive, as dictated by the intended use of the nonwoven fabric. Nonlimiting examples of additives suitable for use in the present disclosure include antimicrobial agents, dyes, opacity enhancers, delustrants, brighteners, skin-care additives, odor control agents, detackifying agents, particulates, preservatives, wetting agents, cleaning agents, detergents, surfactants, silicones, emollients, lubricants, fragrance, fragrance solubilizers, fluorescent whitening agents, UV absorbers, pharmaceuticals, pH control agents, and the like, or combinations thereof.

In an aspect, the nonwoven fabric can be biodegradable, wherein the fiber web comprises natural fibers (e.g., cellulosic fibers).

In aspects where the fiber web comprises natural fibers, the nonwoven fabric can be characterized by a degree of biodegradability of equal to or greater than about 99%, alternatively equal to or greater than about 99.5%, or alternatively equal to or greater than about 99.9%, wherein the degree of biodegradability refers to aerobic biodegradability in soil as determined in accordance with ISO 17556:2003 E. In such aspects, the fiber web can comprise, consist of, or consist essentially of natural fibers. In such aspects, the fiber web can exclude synthetic fibers.

In an aspect, the nonwoven fabric can be characterized by a degree of biodegradability of 100%, wherein the degree of biodegradability refers to aerobic biodegradability in soil as determined in accordance with ISO 17556:2003 E. In such aspect, the fiber web can comprise, consist of, or consist essentially of natural fibers. In such aspect, the fiber web can exclude synthetic fibers.

In an aspect, the nonwoven fabric described herein can comprise the cured cellulosic binder in an amount of from about 0.1 $g/m^2$ to about 10 $g/m^2$, alternatively from about 1 $g/m^2$ to about 9 $g/m^2$, or alternatively from about 2 $g/m^2$ to about 8 $g/m^2$, based on the surface area of the nonwoven fabric.

In an aspect, the nonwoven fabric comprising the cured cellulosic binder as disclosed herein can be characterized by enhanced tensile properties, when compared to an otherwise similar nonwoven fabric that has been treated with a latex-based binder without modified cellulose. As will be appreciated by one of skill in the art, and with the help of this disclosure, the tensile properties of the nonwoven fabric depend upon a variety of factors, such as the type of fibers in the web, the method used for forming the web, the type of binder used, the methods used for applying the binder to the web, curing method for the binder, curing time for the binder, etc. Generally, the integrity of the nonwoven fabric can be assessed by tensile testing, for example by dry tensile strength measured in the machine direction, wet tensile strength measured in the cross direction, and the like, or combinations thereof. Typically, the tensile strength for nonwoven fabrics is measured in cross direction wet strength and machine direction dry strength, but can also be measured in cross direction dry strength and machine direction wet strength.

In an aspect, the nonwoven fabric as disclosed herein can be characterized by a dry tensile strength measured in the machine direction of equal to or greater than about 1,100 grams per linear inch (gli), alternatively equal to or greater than about 1,500 gli, or alternatively equal to or greater than about 2,000 gli, as determined in accordance with EDANA 20.2-89.

In an aspect, the nonwoven fabric as disclosed herein can be characterized by a dry tensile strength measured in the machine direction which can be increased by equal to or greater than about 25%, alternatively equal to or greater than about 30%, or alternatively equal to or greater than about 40% when compared to a dry tensile strength measured in the machine direction of an otherwise similar nonwoven fabric that has been treated with a latex-based binder without modified cellulose, and wherein the tensile strength is determined in accordance with EDANA 20.2-89.

In an aspect, a nonwoven fabric treated with 2.5 wt. % cellulosic binder can be characterized by a dry tensile strength measured in the machine direction which is increased by equal to or greater than about 10%, alternatively equal to or greater than about 30%, or alternatively equal to or greater than about 50% when compared to a dry tensile strength measured in the machine direction of an otherwise similar nonwoven fabric that has been treated with 12 wt. % of a latex-based binder without modified cellulose, and wherein the tensile strength is determined in accordance with EDANA 20.2-89.

In an aspect, the nonwoven fabric as disclosed herein can be characterized by a water wet tensile strength measured in the cross direction of less than about 750 gli, alternatively less than about 400 gli, or alternatively less than about 170 gli, as determined in accordance with EDANA 20.2-89.

In an aspect, the nonwoven fabric as disclosed herein can be characterized by a water wet tensile strength measured in the cross direction which is decreased by equal to or greater than about 25%, alternatively equal to or greater than about 40%, or alternatively equal to or greater than about 50%, when compared to a water wet tensile strength measured in the cross direction of an otherwise similar nonwoven fabric that has been treated with a latex-based binder without modified cellulose, and wherein the tensile strength is determined in accordance with EDANA 20.2-89.

In an aspect, the nonwoven fabric as disclosed herein can be characterized by a mineral oil wet tensile strength measured in the machine direction of equal to or greater than about 1,200 gli, alternatively equal to or greater than about 1,500 gli, or alternatively equal to or greater than about 2,000 gli, as determined in accordance with EDANA 20.2-89.

In an aspect, the nonwoven fabric as disclosed herein can be characterized by a mineral oil wet tensile strength measured in the machine direction which can be increased by equal to or greater than about 25%, alternatively equal to or greater than about 30%, or alternatively equal to or greater than about 40% when compared to a mineral oil wet tensile strength measured in the machine direction of an otherwise similar nonwoven fabric that has been treated with a latex-based binder without modified cellulose, and wherein the tensile strength is determined in accordance with EDANA 20.2-89.

In aspects where the cured cellulosic binder comprises modified cellulose without the binder modifier, the nonwoven fabric can be characterized by an isopropanol wet tensile strength measured in the cross direction of equal to or greater than about 750 gli, alternatively equal to or greater than about 900 gli, or alternatively equal to or greater than about 1,000 gli, as determined in accordance with EDANA 20.2-89.

In aspects where the cured cellulosic binder comprises modified cellulose without the binder modifier, the nonwoven fabric can be characterized by an emulsion wet tensile strength measured in the cross direction of equal to or greater than about 150 gli, alternatively equal to or greater than about 200 gli, or alternatively equal to or greater than about 250 gli, as determined in accordance with EDANA 20.2-89; wherein the emulsion comprises water, an electrolyte, and a solvent selected from the group consisting of glycerol, ethylene glycol, polyethylene glycol, propylene glycol, polypropylene glycol, butylene glycol, and combinations thereof, and wherein the nonwoven fabric is contacted with the emulsion at a weight ratio of emulsion to fabric of about 1:2.

In aspects where the cured cellulosic binder comprises modified cellulose without the binder modifier, the nonwoven fabric can be characterized by an isopropanol wet tensile strength measured in the cross direction which is increased by equal to or greater than about 200%, alternatively equal to or greater than about 250%, alternatively equal to or greater than about 300%, or alternatively equal to or greater than about 350% when compared to an emulsion wet tensile strength measured in the cross direction; wherein the tensile strength is determined in accordance with EDANA 20.2-89; wherein the emulsion comprises water, an electrolyte, and a solvent selected from the group consisting of glycerol, ethylene glycol, polyethylene glycol, propylene glycol, polypropylene glycol, butylene glycol, and combinations thereof, and wherein the nonwoven fabric is contacted with the emulsion at a weight ratio of emulsion to fabric of about 1:2.

In some aspects, the nonwoven fabric as disclosed herein can be used as a substrate for antimicrobial agents, such as alcohols (e.g., ethanol, isopropanol, etc.).

In aspects where the nonwoven fabric further comprises isopropanol, the nonwoven fabric can be antimicrobial, as determined in accordance with ASTM E2315-03(2008) and/or ASTM E1054-08(2013).

In aspects where the nonwoven fabric further comprises isopropanol, the nonwoven fabric can be characterized by at least about 99.9%, alternatively at least about 99.99%, or alternatively 100% efficacy at killing *E. coli* and/or *S. aureus*, as determined in accordance with ASTM E2315-03 (2008) and/or ASTM E1054-08(2013).

For purposes of the disclosure herein, the term "caliper" refers to the thickness of the nonwoven material. The caliper generally refers to the distance between an upper surface and a lower surface of a material, wherein the caliper can be measured under a specified pressure.

In an aspect, the nonwoven fabric as disclosed herein can be characterized by a caliper of equal to or greater than about 0.1 mm, alternatively equal to or greater than about 0.5 mm, alternatively equal to or greater than about 1 mm, alternatively from about 0.1 mm to about 18 mm, alternatively from about 0.1 mm to about 15 mm, alternatively from about 0.1 mm to about 10 mm, alternatively from about 0.5 mm to about 4 mm, or alternatively from about 0.5 mm to about 2.5 mm, as determined in accordance with EDANA 30.5-99.

In an aspect, the nonwoven fabric as disclosed herein can be characterized by a caliper which can be increased by equal to or greater than about 10%, alternatively equal to or greater than about 15%, or alternatively equal to or greater than about 20% when compared to a caliper of an otherwise similar nonwoven fabric that has been treated with a latex-based binder without modified cellulose, wherein the caliper is determined in accordance with EDANA 30.5-99.

Generally, nonwoven materials can exhibit relatively high dust levels, which is typically difficult to control with conventional binder compositions, such as latex binder compositions. Elevated dust levels can be a health concern, as well as an environmental concern.

In an aspect, the nonwoven fabric as disclosed herein can be characterized by a dust level of less than about 5 wt. %, alternatively less than about 4 wt. %, or alternatively less than about 3 wt. %, based on the total weight of the nonwoven fabric. The dust level can be determined by as follows. A nonwoven fabric can be cut in a 11"×8" size sheet and then again cut in strips every ½", parallel to the cross-machine direction; and then the strips can be cut again into ½ lengths. A ½ length nonwoven fabric specimen can be weighed and then placed inside a U.S. Standard Testing Sieve, No. 14. The sieve containing the ½ length nonwoven fabric specimen can be maintained under a vacuum of 30 mm Hg while agitating the nonwoven fabric specimen for about 7 minutes with an agitation nozzle. At the end of the 7 minutes agitation period, the agitation nozzle can be stopped, and the nonwoven fabric specimen can be weighed again. The difference between initial and final weight of nonwoven fabric specimen indicates the dust level of nonwoven fabric.

In an aspect, the nonwoven fabric as disclosed herein can be characterized by a dust level which can be decreased by equal to or greater than about 40%, alternatively equal to or greater than about 50%, or alternatively equal to or greater than about 60% when compared to a dust level of an otherwise similar nonwoven fabric that has been treated with a latex-based binder without modified cellulose.

In an aspect, the nonwoven fabric as disclosed herein can comprise natural fibers (e.g., cellulosic fibers), wherein the nonwoven fabric can be characterized by a dust level which is decreased by equal to or greater than about 99%, alternatively equal to or greater than about 99.5%, or alternatively equal to or greater than about 99.9%, when compared to a dust level of an otherwise similar nonwoven fabric that has not been treated with a binder. In such aspect, the fiber web can comprise, consist of, or consist essentially of natural fibers. In such aspect, the fiber web can exclude synthetic fibers.

In some aspects, nonwovens may be used as a component of a wide variety of absorbent structures, such as surgical drapes and associated materials, diapers, feminine hygiene materials, wipes, mops, and the like. In such aspects, it may be desirable for the nonwovens to have an enhanced water absorbency and/or an enhanced mineral oil absorbency.

In an aspect, the nonwoven fabric as disclosed herein can be characterized by a water absorbency of equal to or greater than about 5 grams of water per gram of nonwoven fabric (g/gm), alternatively equal to or greater than about 7.5 g/gm, or alternatively equal to or greater than about 10 g/gm, as determined in accordance with EDANA 10.3-99.

In an aspect, the nonwoven fabric as disclosed herein can be characterized by a water absorbency which can be increased by equal to or greater than about 50%, alternatively equal to or greater than about 75%, or alternatively equal to or greater than about 100% when compared to a water absorbency of an otherwise similar nonwoven fabric that has been treated with a latex-based binder without modified cellulose, wherein the water absorbency is determined in accordance with EDANA 10.3-99.

In an aspect, the nonwoven fabric treated with 2.5 wt. % cellulosic binder can be characterized by a water absorbency which is increased by equal to or greater than about 50%, alternatively equal to or greater than about 75%, or alternatively equal to or greater than about 100% when compared to a water absorbency of an otherwise similar nonwoven fabric that has been treated with 12 wt. % of a latex-based binder without modified cellulose, and wherein the water absorbency is determined in accordance with EDANA 10.3-99.

In an aspect, the nonwoven fabric as disclosed herein can be characterized by a mineral oil absorbency of equal to or greater than about 5 grams of mineral oil per gram of nonwoven fabric (g/gm), alternatively equal to or greater than about 7.5 g/gm, or alternatively equal to or greater than about 10 g/gm, as determined in accordance with NWSP 010.1.R0 (15).

In an aspect, the nonwoven fabric as disclosed herein can be characterized by a mineral oil absorbency which is increased by equal to or greater than about 25%, alternatively equal to or greater than about 40%, or alternatively equal to or greater than about 50% when compared to a mineral oil absorbency of an otherwise similar nonwoven fabric that has been treated with a latex-based binder without modified cellulose, and wherein the mineral oil absorbency is determined in accordance with NWSP 010.1.R0 (15).

In an aspect, the nonwoven fabric treated with 2.5 wt. % cellulosic binder can be characterized by a mineral oil absorbency which is increased by equal to or greater than about 40%, alternatively equal to or greater than about 60%, or alternatively equal to or greater than about 75% when compared to a mineral oil absorbency of an otherwise similar nonwoven fabric that has been treated with 12 wt. % of a latex-based binder without modified cellulose, and wherein the mineral oil absorbency is determined in accordance with NWSP 010.1.R0 (15).

In some aspects, nonwovens may be used as a component of a wide variety of absorbent structures, such as surgical flushable nonwovens and/or dispersible nonwovens (e.g., flushable wipes, dispersible wipes, etc.). In such aspects, it may be desirable for the nonwovens to have a reduced dispersion time.

In an aspect, the nonwoven fabric as disclosed herein can be characterized by a dispersion time in water of less than about 10 seconds, alternatively less than about 5 seconds, or alternatively less than about 1 second, wherein the dispersion time is determined via a slosh box tester in accordance with GD3 INDA/EDANA. In such aspect, the nonwoven fabric can comprise a cellulosic binder without a wet strength agent. In such aspects, the nonwoven fabric can exclude a wet strength agent. For purposes of the disclosure herein, the term "dispersion time" refers to a measure of dispersibility of nonwovens. Further, for purposes of the disclosure herein, the term "dispersibility" refers to the physical separation of nonwovens into smaller pieces. The dispersion time in water increases with increasing the amount of crosslinking agent in the cured cellulosic binder. As will be appreciated by one of skill in the art, and with the help of this disclosure, and without wishing to be limited by theory, an increased amount of crosslinking agent leads to an increased number of covalent bonds between the crosslinking agent, and both the modified cellulose and the fiber web (e.g., cellulosic fibers of the fiber web), which in turn delays the breaking down of the nonwoven.

In an aspect, the nonwoven fabric can comprise a wet strength agent, wherein the nonwoven fabric is characterized by no dispersion (e.g., is substantially free of dispersion, is characterized by substantially no dispersion, etc.), wherein the dispersion is determined via a slosh box tester in accordance with GD3 INDA/EDANA. The dispersion time in water increases with increasing the amount of wet strength agent in the cured cellulosic binder. As will be appreciated by one of skill in the art, and with the help of this disclosure, and without wishing to be limited by theory, an increased amount of wet strength agent leads to an increased number of chemical bonds (e.g., ionic bonds, covalent bonds) between the wet strength agent, and both the modified cellulose and the fiber web, which in turn delays the breaking down of the nonwoven.

In an aspect, the nonwoven fabric comprising the cured cellulosic binder as disclosed herein can be formed into any suitable article of manufacture by using any suitable methodology. Nonlimiting examples of articles that can be formed from the nonwoven fabrics of the present disclosure include wipes, moisturized wipes, tissues, towels, moisturized tissue towels (MTT), double re-creped (DRC) items, seed blankets, agricultural wraps, agricultural blankets, medical drapes, bandages, caps, face masks, surgical scrubs, medical gowns, filters, diapers, padding, packaging, insulation, carpeting, upholstery, fabric dryer sheets, disposable textiles, earphone protection covers, insulation, wall coverings, and the like, or combinations thereof.

In an aspect, the wipes can comprise industrial wipes, disinfection wipes, flushable wipes (e.g., water flushable wipes), dispersible wipes (e.g., water dispersible wipes), and the like, or combinations thereof.

In an aspect, an aqueous cellulosic binder can comprise modified cellulose, a crosslinking agent, and water; wherein the modified cellulose comprises CMC and/or sodium CMC; wherein the aqueous cellulosic binder can be characterized by a weight ratio of water to modified cellulose of from about 50:1 to about 10:1; wherein the aqueous cellulosic binder can be characterized by a weight ratio of crosslinking agent to modified cellulose of from about 1:5 to about 1:100; wherein the aqueous cellulosic binder can comprise the modified cellulose in an amount of from about 2.5 wt. % to about 25 wt. %; and wherein the aqueous cellulosic binder is a sprayable aqueous solution. In such aspect, the crosslinking agent can comprise citric acid; and the aqueous cellulosic binder can further comprise a softening agent in an amount of from about 1 wt. % to about 2.5 wt. %, wherein the softening agent is polyethylene glycol.

In an aspect, a method of making an aqueous cellulosic binder can comprise the steps of (a) contacting modified cellulose with water to form a modified cellulose solution, wherein the modified cellulose comprises CMC and/or sodium CMC, wherein the modified cellulose solution can comprise the modified cellulose in an amount of from about 2.5 wt. % to about 25 wt. %; and (b) contacting at least a portion of the modified cellulose solution with a crosslinking agent to form the aqueous cellulosic binder, wherein the crosslinking agent comprises a carboxylic acid having two or more carboxyl groups, wherein the aqueous cellulosic binder can be characterized by a weight ratio of water to modified cellulose of from about 50:1 to about 10:1; and wherein the aqueous cellulosic binder can be characterized by a weight ratio of crosslinking agent to modified cellulose of from about 1:5 to about 1:100. In such aspect, the crosslinking agent can comprise citric acid. In such aspect, the method of making an aqueous cellulosic binder can further comprise a step of contacting the aqueous cellulosic binder (already containing the crosslinking agent) with an additive comprising a softening agent, wherein the softening agent is polyethylene glycol, and wherein the softening agent is present in the aqueous cellulosic binder in an amount of from about 1 wt. % to about 2.5 wt. %.

In an aspect, a method of making a nonwoven fabric can comprise the steps of (a) forming a plurality of fibers into a fiber web via an airlaid process, wherein the plurality of fibers consist essentially of cellulosic fibers; (b) spraying at least a portion of the fiber web with an aqueous cellulosic binder to form a binder impregnated fiber web; wherein the aqueous cellulosic binder can comprise modified cellulose, a crosslinking agent, and water; wherein the modified cellulose comprises CMC and/or sodium CMC; wherein the aqueous cellulosic binder can be characterized by a weight ratio of water to modified cellulose of from about 50:1 to about 10:1; wherein the aqueous cellulosic binder can be characterized by a weight ratio of crosslinking agent to modified cellulose of from about 1:5 to about 1:100; wherein the aqueous cellulosic binder can comprise the modified cellulose in an amount of from about 2.5 wt. % to about 25 wt. %; and wherein the aqueous cellulosic binder is a sprayable aqueous solution; and (c) curing the binder impregnated fiber web at temperature of from about 110° C. to about 220° C. to form the nonwoven fabric, wherein the nonwoven fabric comprises a cured cellulosic binder, and wherein the cured cellulosic binder comprises at least a portion of the modified cellulose of the aqueous cellulosic binder and at least a portion of the crosslinking agent of the aqueous cellulosic binder.

In an aspect, a nonwoven fabric can comprise nonwoven fibrous material chemically bound with a modified cellulose-based binder, wherein the modified cellulose-based binder comprises CMC and/or sodium CMC crosslinked with citric acid, and wherein the nonwoven fibrous material can comprise a fiber web as disclosed herein and a cured cellulosic binder as disclosed herein. In such aspect, the modified cellulose-based binder further comprises a wet strength agent that chemically binds the nonwoven fibrous material; wherein the wet strength agent comprises at least one reactive functional group selected from the group consisting of a halide group, a chloride group, a fluoride group, a hydroxyl group, and combinations thereof. The fiber web can be present in the nonwoven fabric in an amount of from about 85 wt. % to about 99.9 wt. %, and the cured cellulosic binder can be present in the nonwoven fabric in an amount of from about 0.1 wt. % to about 15 wt. %, based on the total weight of the nonwoven fabric. In such aspect, the cured cellulosic binder can comprise the modified cellulose and citric acid in a weight ratio of citric acid to modified cellulose of from about 1:5 to about 1:100.

In an aspect, a nonwoven fabric as disclosed herein can comprise a fiber web in an amount of from about 85 wt. % to about 99.9 wt. %, based on the total weight of the nonwoven fabric; and a cured cellulosic binder in an amount of from about 0.1 wt. % to about 15 wt. %, based on the total weight of the nonwoven fabric, wherein the fiber web consists essentially of cellulosic fibers, wherein the cured cellulosic binder comprises modified cellulose and a crosslinking agent in a weight ratio of crosslinking agent to modified cellulose of from about 1:5 to about 1:100. In such aspect, the nonwoven fabric can be characterized by a dry tensile strength that is increased by equal to or greater than about 25%, a water wet tensile strength that is decreased by equal to or greater than about 25%, a mineral oil wet tensile strength that is increased by equal to or greater than about 25%, a caliper that is increased by equal to or greater than about 10%, a water absorbency that is increased by equal to or greater than about 50%, and a mineral oil absorbency that is increased by equal to or greater than about 25%, when compared to the respective properties of an otherwise similar nonwoven fabric that has been treated with a latex-based binder without modified cellulose; wherein the tensile strength is determined in accordance with EDANA 20.2-89; wherein the caliper is determined in accordance with EDANA 30.5-99; wherein the water absorbency is determined in accordance with EDANA 10.3-99; and wherein the mineral oil absorbency is determined in accordance with NWSP 010.1.R0 (15). In such aspect, the nonwoven fabric is characterized by a degree of biodegradability of equal to or greater than about 99%, wherein the degree of biodegradability refers to aerobic biodegradability in soil as determined in accordance with ISO 17556:2003 E.

In an aspect, the cellulosic binder compositions and methods of making and using same, as well as nonwoven fabrics and methods of making same as disclosed herein can advantageously display improvements in one or more composition characteristics when compared to conventional latex-based binder compositions and methods of making and using same, as well as conventional nonwoven fabrics and methods of making same, respectively. About a million tons conventional latex binders are often applied into nonwoven fabric annually. In conventional nonwoven fabric manufacturing processes, about 15% to 26% latex binder is required to achieve the desired properties of nonwoven fabric. Conventional latex binders are fairly expensive (about $3,000/MT) and can contribute to environmental concerns. The cellulosic binders as disclosed herein are much cheaper than latex binders, and can be applied in significantly lower amounts (about 2% to 2.5%), thereby resulting in a huge manufacturing cost savings. As will be appreciated by one of skill in the art and with the help of this disclosure, petroleum-based melt bonding materials such as plastic fibers or chemical bonding agents such as latex binders are about three times as expensive when compared to cellulosic pulp fiber. Additionally, large volumes of latex binder are required to achieve the minimum quality target for nonwovens, leading to the use of latex-based binders being more costly.

In an aspect, the environmental impact of reducing or eliminating the use of latex-based binders can be advantageous, as emissions linked to the volatile byproducts of the latex binder can pose environmental and health concerns.

In an aspect, the cellulosic binder as disclosed herein is a natural binder that is advantageously both biodegradable and formaldehyde-free (e.g., environmentally friendly).

In an aspect, the cellulosic binder as disclosed herein can be advantageously used in small amounts as compared to latex binders. In such aspect, the natural binder treated nonwovens can display significantly increased dry strength, wet strength, mineral oil wet strength, softness, water and oil absorbency, and water dispersibility, as well as significantly decreased dust level. In such aspect, the natural binder treated nonwovens can advantageously display reduced environmental and health concerns as compared to latex binder treated nonwoven fabrics.

In an aspect, the cellulosic binder as disclosed herein is a natural binder, which can advantageously exclude latex, acrylamide, formaldehyde, and other synthetic ingredients commonly used in conventional synthetic latex binders. The modified cellulose (e.g., CMC and/or sodium CMC) and the crosslinking agent (e.g., (citric acid) are natural based products, minimally modified. The cellulosic binder as disclosed herein can be advantageously made from food grade ingredients, such as CMC and/or sodium CMC, citric acid, as well as a softening agent, which can be polyethylene glycol, a compound used for human consumption to alleviate constipation. The use of natural based ingredients in the cellulosic binder as disclosed herein can advantageously allow for the cellulosic binder to be biodegradable, as opposed to the conventional latex-based binders which are not biodegradable.

In an aspect, the cellulosic binder as disclosed herein can advantageously allow for significantly reducing nonwovens dispersion time as well as increasing absorbency of the nonwoven fabric. The nonwovens comprising a cured cellulosic binder as disclosed herein can be advantageously easily dispersible in water, as opposed to nonwovens comprising conventional latex-based binders, which are not easily dispersible in water.

In an aspect, the nonwovens comprising a cured cellulosic binder as disclosed herein can advantageously display increased strength and decreased dust levels when compared to nonwovens comprising conventional latex-based binders. An improvement in dust level can reduce the environmental and health hazard impact of the nonwoven manufacturing process. As will be appreciated by one of skill in the art, and with the help of this disclosure, conventional nonwoven fabrics are generally characterized by high dust levels, which is a concern in nonwovens manufacturing.

In an aspect, the cellulosic binder as disclosed herein can be advantageously used in airlaid nonwovens, wherein the cellulosic binder is a modified cellulose-based natural binder. The cellulosic binder as disclosed herein can be advantageously used as an alternative to conventional latex-based binders for making the nonwoven fabric which is conventionally known as LBAL (latex bond) nonwoven fabric when the latex binder is used. The cellulosic binder as disclosed herein can be advantageously used as a binder in MBAL (multi-bonded) nonwoven fabric and/or TBAL (thermal-bonded) nonwoven fabric. Additional advantages of the cellulosic binder compositions and methods of making and using same, as well as nonwoven fabrics and methods of making same as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner. All composition % are wt. %, unless otherwise specified herein.

Example 1

Cellulosic binder compositions were prepared and used as follows. Modified cellulose (e.g., CMC and/or sodium CMC) was dissolved in water to produce a modified cellulose solution. Citric acid and polyethylene glycol were added to the modified cellulose solution to form the aqueous cellulosic binder compositions. 1 liter of cellulosic binder sample #1 was prepared by using 30 g CMC, 5 g citric acid, 15 g polyethylene glycol, and 950 g water. 1 liter of cellulosic binder sample #2 was prepared by using 30 g CMC, 10 g citric acid, 15 g polyethylene glycol, and 945 g water. 1 liter of cellulosic binder sample #3 was prepared by using 30 g CMC, 15 g citric acid, 15 g polyethylene glycol, and 940 g water. In each case, the modified cellulose, citric acid, and polyethylene glycol were dissolved in water separately, to yield the modified cellulose solution, citric acid solution, and polyethylene glycol solution, respectively. Further, both the citric acid solution and the polyethylene glycol solution were blended into the modified cellulose solution, and then the blended product was stirred for 30 minutes at room temperature to form the aqueous cellulosic binder composition.

Hand sheets (nonwoven fabric) were prepared with a hand sheet molding machine, and the hand sheets were subjected to testing to determine properties such as tensile strength properties, absorbency, caliper, and dispersibility. Each cellulosic binder sample was sprayed on the surface of the fiber web (i.e., 100 wt. % pulp fiber web; 80 wt. % pulp fiber and 20 wt. % bicomponent fiber web; or 70 wt. % pulp fiber and 30 wt. % bicomponent fiber web, based on the weight of the fiber web) with a spray machine.

The properties of the nonwovens are displayed in Table 1. Further, a conventional latex binder (e.g., ELITE 22 binder; vinyl acetate ethylene (VAE) latex binder), was used for comparison purposes. ELITE 22 binder is a vinyl acetate ethylene emulsion based on the copolymerization of vinyl acetate and ethylene, in which the vinyl acetate content can range between 60% and 95%, and the ethylene content can range between 5% and 40% percent of the total polymeric formulation. ELITE 22 binder is commercially available from Celanese Emulsions, Bridgewater, NJ The novelty of the natural cellulosic binder composition as disclosed herein is that such binder contains ingredients that are natural, biodegradable, formaldehyde-free, inexpensive, etc. Further, the natural cellulosic binder composition as disclosed herein can be applied in very low amounts (in some aspects only require about 2-2.5% natural binder addition) to fiber webs for forming nonwoven fabrics, while latex-based EVA binders need about 15-26% application onto fiber webs for forming nonwoven fabrics; which may significantly reduce the overall production cost of nonwoven fabrics, along with lowering or eliminating environmental and health concerns for natural cellulosic binder compositions.

Example 2

Cellulosic binder compositions were prepared as disclosed in Example 1 and were used as follows. As will be appreciated by one of skill in the art, and with the help of this disclosure, and without wishing to be limited by theory, the viscosity of CMC solutions depends on the molecular weight of CMC, as well as electrolyte content of the CMC solutions. The cellulosic binder compositions of Example 2 were prepared based on three different types of CMC having varying degrees of viscosity (e.g., high viscosity, medium viscosity, and low viscosity). All three different types of CMC were dissolved in water separately. A portion of each of the resulting medium viscosity CMC aqueous solution and low viscosity CMC aqueous solution was individually further contacted separately with an electrolyte ($CaCl_2$), and with a wet strength agent (POLYCUP 2000 crosslinking resin, which is polyacrylamide epichlorohydrin (PAE) available from Solenis) to form the aqueous cellulosic binder. The solid weight ratio of CMC to wet strength agent was 2:0.3 (i.e., 20:3). Further, a conventional latex binder (e.g., ELITE 22 binder) was used for comparison purposes.

Each cellulosic binder sample was sprayed on the surface of a fiber web (100% pulp fiber web, based on the weight of the fiber web) with a spray machine.

The nonwovens were subjected to testing to determine properties such as tensile strength properties, absorbency, caliper, dust level, and dispersibility; and these properties are displayed in Tables 2, 3, and 4. Table 2 displays the physical properties of hand sheet nonwoven products prepared with different viscosity cellulosic binder. Hand sheets (nonwoven fabric) were prepared with a hand sheet molding machine. Table 3 displays the physical properties of non-

TABLE 1

| Nonwoven sample # (corresponding to the binder sample #) | Basis weight (gm) | Binder Add on % | Caliper (mm) | Dry Strength (gli) | Wet Strength (gli) | Mineral Oil Wet Strength (gli) | Mineral Oil Absorption Capacity (g/gm) | Water Absorption Capacity (g/gm) | Dispersion Time In Water (sec) |
|---|---|---|---|---|---|---|---|---|---|
| 1 | 55 | 2.5 | 0.9 | 880 | 170 | 915 | 10.0 | 12.00 | Slowly disperse |
| 2 | 55 | 2.5 | 0.9 | 875 | 280 | 895 | 10.3 | 12.5 | Very slowly disperse |
| 3 | 55 | 2.5 | 0.9 | 925 | 415 | 938 | 10.0 | 11.0 | Not disperse |
| 3 | 75 | 2.5 | 0.9 | 1310 | 740 | 1350 | 9.5 | 11.0 | Not disperse |
| ELITE 22 binder (Comparison) | 55 | 12 | 0.9 | 610 | 270 | 622 | 7.5 | 8.5 | Never disperse | woven products prepared with low viscosity cellulosic binder, wherein the nonwovens were produced with only pulp fiber. Table 4 displays the physical properties of nonwoven TBAL (thermal-bonded) nonwoven fabric products treated with cellulosic binder, wherein the TBAL nonwovens were produced with both pulp and bicomponent fiber.

treated nonwoven fabric, but the wet strength of cellulosic binder treated nonwoven fabric was low. Consequently, cellulosic binder treated nonwoven fabric could be used for industrial and/or disinfection wipes, as well as for water flushable and/or dispersible wipe. However, the wet strength of cellulosic binder treated nonwoven fabric can be

TABLE 2

| Binder | Basis weigh (gm) | Binder Add on % | Caliper (mm) | Dry Strength (gli) | Wet Strength (gli) | Mineral Oil Wet Strength (gli) | Water Absorption Capacity (gm) | Water Absorption rate (Sec) | Dispersion Time In Water (sec) |
|---|---|---|---|---|---|---|---|---|---|
| High viscosity cellulosic binder | 50 | 2 | 0.45 | 2234 | 55 | 2250 | 12.0 | 1 | 1 |
| Medium viscosity cellulosic binder | 50 | 2.5 | 0.5 | 2735 | 36 | 2698 | 12.0 | 1 | 1 |
| Medium viscosity cellulosic binder with wet strength agent | 50 | 2.5 | 0.5 | 2321 | 235 | 2410 | 12.5 | 1 | Not Disperse |
| Low viscosity Cellulosic Binder | 50 | 2.5 | 0.47 | 946 | 45 | 950 | 13.0 | 1 | 1 |
| Low viscosity Cellulosic Binder with Wet Strength agent | 50 | 2.5 | 0.41 | 944 | 370 | 980 | 12.9 | 1 | Not Disperse |
| Low viscosity Cellulosic Binder with CaCl$_2$ | 50 | 2.5 | 0.48 | 1050 | 52 | 1100 | 11.2 | 1 | 1 |
| Latex Binder (ELITE 22 binder) | 50 | 12 | 0.43 | 1092 | 490 | 1052 | 8.0 | 2.3 | Never Disperse |

TABLE 3

| Binder | Basis weight (gm) | Binder Add on % | Caliper (mm) | Dry Strength (gli) | Wet Strength (gli) | Mineral Oil Wet Strength (gli) | Mineral Oil Absorption Capacity (g/gm) | Mineral Oil Absorption Rate (Sec) | Water Absorption Capacity (g/gm) | Absorption Rate (Sec) | Brightness Index | Dispersion in Water (sec) |
|---|---|---|---|---|---|---|---|---|---|---|---|---|
| Low viscosity cellulosic binder | 50 | 3.0 | 0.48 | 1364 | 29 | 1129 | 10.0 | 47 | 12.53 | 2.5 | 86 | 1 |
| Low viscosity cellulosic binder | 50 | 2.5 | 0.5 | 1162 | 28 | 1226 | 11.3 | 45 | 13.3 | 2.0 | 86 | 1 |
| Low viscosity cellulosic binder | 60 | 2.0 | 0.59 | 871 | 30 | 733 | 10.4 | 45 | 13.38 | 2.0 | 86 | 1 |
| Latex binder (ELITE 22 binder) | 50 | 12 | 0.43 | 1008 | 497 | 982 | 7.8 | 112 | 8.0 | 2.3 | 85 | Never disperse |

TABLE 4

| Cellulosic Binder | Machine Direction (MD) Dry Strength (gli) | | Cross Direction (CD) Wet Strength (gli) | | Dust Level |
|---|---|---|---|---|---|
| Add on % | Strength | Elongation | Strength | Elongation | % |
| No Binder | 822.0 | 20.1 | 542.4 | 36.65 | 22.4 |
| 0.5% | 1063.0 | 10.6 | 599.4 | 17.6 | 5.9 |
| 1.0% | 1207.3 | 8.7 | 647.3 | 12.1 | 2.9 |

The optimum cellulosic binder add on percentage was found to be about 2.5%, based on tensile strength properties, absorbency, and other physical properties of nonwoven fabric.

The data in Tables 2 and 3 indicate that the dry tensile strength and oil and alcohol wet tensile strength of 2.5% cellulosic binder treated nonwoven fabric was significantly higher than the corresponding properties of 12% latex binder increased with the addition of a wet strength agent (Table 2); and these data indicate that cellulosic binder treated nonwoven fabric having a wet strength agent could be used as a replacement for latex binder treated airlaid nonwovens.

The data in Table 4 indicate that the cellulosic binder may be used in MBAL (multi-bonded) nonwoven fabric and/or TBAL (thermal-bonded) nonwoven fabric products.

The MBAL product was also produced with 75 wt. % pulp fiber, 20 wt. % bicomponent fiber and 5 wt. % latex binder, based on the weight of the final MBAL product; and TBAL product was also produced with 69 wt. % pulp fiber and 31 wt. % bicomponent fiber. As will be appreciated by one of skill in the art, and with the help of this disclosure, both latex binder and bicomponent fiber are expensive. Further, and as will be appreciated by one of skill in the art, and with the help of this disclosure, latex binder and plastic materials have health and environmental concerns associated with, due to their often non-biodegradable nature, emissions (e.g., formaldehyde emissions), etc. The application of a small amount (1% add on) of natural binder instead of latex binder into MBAL or TBAL products could significantly improve physical properties of nonwoven fabrics (e.g., especially tensile strength), which in turn could reduce bicomponent fiber and latex binder usage; and could replace the latex binder, which could reduce significantly production cost, as well as alleviate health and environmental concerns.

Example 3

Cellulosic binder compositions were prepared and used as disclosed in Examples 1 and 2. Cellulosic binder compositions were prepared in five different ways, as follows: (1) modified cellulose (e.g., CMC and/or sodium CMC) was dissolved in water to produce a modified cellulose solution; (2) polyethylene glycol solution (softening agent) was blended with the modified cellulose solution; (3) citric acid (crosslinking agent) was dissolved in water and then blended with the modified cellulose solution; (4) citric acid solution and polyethylene glycol solution were blended with the modified cellulose solution, and (5) modified cellulose solution was blended with a wet strength agent and a softening agent. Approximately 2.5% add on of the cellulosic binder compositions (all-natural binder) (1) through (5) were individually sprayed on both surfaces of the fiber web of nonwoven fabric (each binder composition was sprayed on a different piece of nonwoven fabric), and then were cured at 160° C. for physical properties testing. As a result, the dry strength, oil wet strength, water and mineral oil absorbency, softness, and dispersibility in water of nonwoven fabric treated with the cellulosic binder compositions (1) and (2) (natural binder) was shown to be significantly higher than that of nonwoven fabric treated similarly with 12% latex binder (ELITE 22 binder). However, the water wet strength of nonwoven fabric treated with the cellulosic binder compositions (1) and (2) (natural binder) was significantly lower than that of nonwoven fabric treated similarly with 12% latex binder (ELITE 22 binder). Further, the dry strength, wet strength, oil wet strength, softness, water and mineral oil absorbency of nonwoven fabric treated with the cellulosic binder compositions (3), (4) and (5) (natural binder) was shown to be significantly higher than that of nonwoven fabric treated similarly with 12% latex binder (ELITE 22 binder). Furthermore, the water dispersibility of the natural binder (e.g., cellulosic binder compositions as disclosed herein) treated nonwoven fabric decreased with increasing the concentration of crosslinking agent or wet strength agent into natural binder. Additionally, the dust level of all-natural binder treated nonwoven fabric was significantly lower than that of nonwoven fabric treated similarly with 12% latex binder (ELITE 22 binder).

Example 4

Cellulosic binder compositions were prepared and used as follows. Modified cellulose (e.g., CMC and/or sodium CMC) was dissolved in water to produce a cellulosic binder solution for machine trial. 1,000 kg of cellulosic binder sample #4 was prepared by using 30 kg CMC and 970 kg water. 1,000 kg of cellulosic binder sample #5 was prepared by using 30 kg CMC, 15 kg citric acid and 955 kg water. 1,000 kg of cellulosic binder sample #6 was prepared by using 30 kg CMC, 4 kg (solid) wet strength agent (POLYCUP 2000 (POLYCUP crosslinking resin, which is polyacrylamide epichlorohydrin (PAE) available from Solenis) and 96 kg water.

The nonwoven fabrics were produced by using a conventional nonwoven production machine with three different amounts of cellulosic binder (e.g., add on percent): 2.5%, 3.0%, and 3.5%; and then the binder-treated fabric sheets were subjected to testing to determine properties such as tensile strength properties, absorbency, caliper, dispersibility, disinfecting/antimicrobial properties with alcohol (e.g., isopropanol or isopropyl alcohol (IPA)), and wet strength with an emulsion (e.g., an alcohol and solvent-based emulsion). The solvent-based emulsion was prepared with 35% ethylene glycol, 10% glycerin, 1% $CaCl_2$, and 54% water, and the fabric to emulsion weight ratio was 1:2. The disinfecting/antimicrobial properties of the nonwoven products were investigated by challenging the nonwoven fabrics with different bacterial species for a specified amount of time and temperature to determine the percent (%) or log 10 reduction from an initial microbial population, in accordance with ASTM E2315-03(2008) and/or ASTM E1054-08(2013). The bacteria was *Staphylococcus aureus* (*S. aureus*) ATCC6538™ and *Escherichia Coli* (*E. coli*) ATCC8739™, which were purchased from Microbiologics®. Each cellulosic binder sample was sprayed on the surface of the fiber web (i.e., 100 wt. % pulp fiber webs) with a spray machine and cured at 110° C.-220° C. inside a machine dryer.

Tables 5, 6 and 7 display the results of the experiments for the three different cellulosic binder samples: #4, #5, and #6. Table 5 displays physical properties of machine trial for the nonwoven fabric treated with cellulosic binder samples: #4, #5, and #6. Table 6 displays wet strength properties of solvent-based emulsion treated nonwoven fabrics (cellulosic binder samples: #4). Table 7 displays disinfecting/antimicrobial properties: log 10 reduction results for the Time Kill Test on the isopropanol (IPA) solution the nonwoven fabric treated with cellulosic binder samples: #4, #5, and #6.

TABLE 5

| Nonwoven machine trial sample # (corresponding to the binder sample #) | Basis weight (gm) | Binder Add on % | Caliper (mm) | MD Dry Strength (gli) | CD Dry Strength (gli) | CD Wet Strength (gli) | Water Absorption Capacity (g/gm) | Dispersibility Time In Water (sec) |
|---|---|---|---|---|---|---|---|---|
| 4 | 60 | 2.5 | 0.6 | 1020 | 962 | 25 | 11.0 | 1 |
| 4 | 60 | 3.0 | 0.6 | 1120 | 964 | 29 | 11.8 | 1 |
| 4 | 60 | 3.5 | 0.6 | 1190 | 1028 | 27 | 11.0 | 1 |
| 5 | 55 | 2.5 | 0.5 | 968 | 720 | 170 | 10.5 | Not disperse |
| 5 | 55 | 3.0 | 0.5 | 1014 | 819 | 190 | 10.0 | Not disperse |
| 5 | 55 | 3.5 | 0.5 | 1067 | 850 | 207 | 11.0 | Not disperse |
| 6 | 55 | 2.5 | 0.6 | 1435 | 870 | 280 | 11.0 | Not disperse |

TABLE 5-continued

| Nonwoven machine trial sample # (corresponding to the binder sample #) | Basis weight (gm) | Binder Add on % | Caliper (mm) | MD Dry Strength (gli) | CD Dry Strength (gli) | CD Wet Strength (gli) | Water Absorption Capacity (g/gm) | Dispersibility Time In Water (sec) |
|---|---|---|---|---|---|---|---|---|
| 6 | 55 | 3.0 | 0.6 | 1480 | 964 | 319 | 10.5 | Not disperse |
| 6 | 55 | 3.5 | 0.6 | 1502 | 1102 | 350 | 11.2 | Not disperse |
| ELITE 22 latex binder-grade 6803 (Comparison) | 55 | 12.0 | 0.5 | 710 | 650 | 303 | 8.2 | Not disperse |

TABLE 6

| Nonwoven machine trial sample # (corresponding to the binder sample #) | Basis weight (gm) | Binder Add on % | Caliper (mm) | CD Wet Strength with Alcohol (IPA) (gli) | CD Wet Strength in Solvent-Based Emulsion (gli) | Dispersibility Time in Water (sec) |
|---|---|---|---|---|---|---|
| 4 | 60 | 2.5 | 0.6 | 1050 | 280 | 2 |
| 4 | 60 | 3.0 | 0.6 | 1100 | 300 | 2 |
| 4 | 60 | 3.5 | 0.6 | 1215 | 310 | 2 |

TABLE 7

|  | Substrate with IPA Lotion: A | Substrate with IPA Lotion: B | Substrate with IPA Lotion: C |
|---|---|---|---|
| *Staphylococcus aureus* (*S. aureus*) ATCC ®6538 ™ | | | |
| 10 seconds | 6.048 | 4.872 | 6.048 |
| 30 seconds | 6.048 | 4.872 | 6.048 |
| 60 seconds | 6.048 | 6.048 | 6.048 |
| 4 minutes | 6.048 | 6.048 | 6.048 |
| *Escherichia Coli* (*E. coli*) ATCC ®8739 ™ | | | |
| 10 seconds | 6.089 | 6.089 | 6.089 |
| 30 seconds | 6.089 | 6.089 | 6.089 |
| 60 seconds | 6.089 | 6.089 | 6.089 |
| 4 minutes | 6.089 | 6.089 | 6.089 |

A = nonwoven fabric substrate comprising cellulosic binder sample #4; B = nonwoven fabric substrate comprising cellulosic binder sample #5; C = nonwoven fabric substrate comprising cellulosic binder sample #6.

The data in Table 5 showed that in the absence of a crosslinking agent or a wet strength agent, the nonwoven fabric treated with cellulosic binder sample #4 displayed very low wet strength, such as less than 50 gli and the fabric easily dispersed in water. However, when the fabric was treated with crosslinking agent (cellulosic binder sample #5) or a wet strength agent (cellulosic binder sample #6), the wet strength of the nonwoven fabric was increased up to 350 gli and the fabric did not disperse in water. The data in Table 6 indicated that in the absence of a crosslinking agent or a wet strength agent, the nonwoven fabric treated with cellulosic binder sample #4 displayed significant wet strength when sprayed with alcohol or solvent-based emulsion on the fabric surface. The data in Table 7 showed that the alcohol with fabric (A) killed 100% bacteria, alcohol with fabric (B) killed 99.99% bacteria, and alcohol with fabric (C) killed 100% bacteria; thus indicating that the nonwoven fabrics as disclosed herein are suitable substrates for disinfectant/antimicrobial products.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

Additional Disclosure

A first aspect, which is an aqueous cellulosic binder comprising modified cellulose, water, and optionally a crosslinking agent; wherein the aqueous cellulosic binder is characterized by a weight ratio of water to modified cellulose of from about 99.9:0.1 to about 1,000:500; wherein, when the crosslinking agent is present, the aqueous cellulosic binder is characterized by a weight ratio of crosslinking agent to modified cellulose of from about 1:2 to about 1:1,000; wherein the modified cellulose comprises CMC and/or sodium CMC; and wherein the crosslinking agent comprises a carboxylic acid having two or more carboxyl groups.

A second aspect, which is the aqueous cellulosic binder of the first aspect, wherein the aqueous cellulosic binder is a sprayable aqueous solution.

A third aspect, which is the aqueous cellulosic binder of any one of the first and the second aspects, wherein the carboxylic acid having two or more carboxyl groups comprises citric acid, oxalic acid, malonic acid, succinic acid, glutaric acid, adipic acid, malic acid, polyacrylic acid, or combinations thereof.

A fourth aspect, which is the aqueous cellulosic binder of any one of the first through the third aspects, wherein the aqueous cellulosic binder comprises the modified cellulose in an amount of from about 0.1 wt. % to about 50 wt. %.

A fifth aspect, which is the aqueous cellulosic binder of any one of the first through the fourth aspects, wherein the aqueous cellulosic binder comprises the crosslinking agent in an amount of from about 0.1 wt. % to about 10 wt. %.

A sixth aspect, which is the aqueous cellulosic binder of any one of the first through the fifth aspects further comprising a wet strength agent in an amount of from about 0.1 wt. % to about 10 wt. %; wherein the wet strength agent comprises at least one reactive functional group selected from the group consisting of a halide group, a chloride group, a fluoride group, a hydroxyl group, and combinations thereof.

A seventh aspect, which is the aqueous cellulosic binder of the sixth aspect, wherein the wet strength agent comprises N-methylolacrylamide (NMA), polyacrylamide (PAM), glyoxylated polyacrylamide (GPAM), polyamide epichlorohydrin (PAE) (e.g., (POLYCUP 2000 (POLYCUP crosslinking resin, which is polyacrylamide epichlorohydrin (PAE) available from Solenis)), polyamidoamine epichlorohydrin (PAAE), or combinations thereof.

An eighth aspect, which is the aqueous cellulosic binder of any one of the first through the seventh aspects further comprising a softening agent in an amount of from about 0.1 wt. % to about 10 wt. %.

A ninth aspect, which is the aqueous cellulosic binder of the eighth aspect, wherein the softening agent comprises an anionic surfactant, glycerol, a polyethylene emulsion, ethylene glycol, polyethylene glycol, propylene glycol, polypropylene glycol, butylene glycol, a fatty alcohol ethoxylate, sodium lauryl sulfate, a silicone-based softener, a nanomaterials-based softener, or combinations thereof.

A tenth aspect, which is the aqueous cellulosic binder of any one of the first through the ninth aspects further comprising an electrolyte in an amount of from about 0.1 wt. % to about 10 wt. %.

An eleventh aspect, which is the aqueous cellulosic binder of the tenth aspect, wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

A twelfth aspect, which is the aqueous cellulosic binder of any one of the first through the eleventh aspects, wherein the aqueous cellulosic binder is biodegradable.

A thirteenth aspect, which is the aqueous cellulosic binder of any one of the first through the twelfth aspects, wherein the aqueous cellulosic binder is characterized by a degree of biodegradability of equal to or greater than about 99%, and wherein the degree of biodegradability refers to aerobic biodegradability in soil as determined in accordance with ISO 17556:2003 E.

A fourteenth aspect, which is a cellulosic binder comprising modified cellulose and a crosslinking agent in a weight ratio of crosslinking agent to modified cellulose of from about 1:2 to about 1:1,000, wherein the modified cellulose comprises CMC and/or sodium CMC, and wherein the crosslinking agent comprises a carboxylic acid having two or more carboxyl groups.

A fifteenth aspect, which is the cellulosic binder of the fourteenth aspect further comprising water.

A sixteenth aspect, which is the cellulosic binder of the fifteenth aspect, wherein the cellulosic binder is characterized by a weight ratio of water to modified cellulose of from about 99.9:0.1 to about 1,000:500.

A seventeenth aspect, which is the cellulosic binder of any one of the fourteenth through the sixteenth aspects, wherein the cellulosic binder is a sprayable aqueous solution.

An eighteenth aspect, which is a cellulosic binder comprising modified cellulose and a wet strength agent in a weight ratio of wet strength agent to modified cellulose of from about 1:2 to about 1:1,000, wherein the modified cellulose comprises CMC and/or sodium CMC, and wherein the wet strength agent comprises at least one reactive functional group selected from the group consisting of a halide group, a chloride group, a fluoride group, a hydroxyl group, and combinations thereof.

A nineteenth aspect, which is the cellulosic binder of the eighteenth aspect further comprising water.

A twentieth aspect, which is the cellulosic binder of the nineteenth aspect, wherein the cellulosic binder is characterized by a weight ratio of water to modified cellulose of from about 99.9:0.1 to about 1,000:500.

A twenty-first aspect, which is the cellulosic binder of any one of the eighteenth through the twentieth aspects, wherein the cellulosic binder is a sprayable aqueous solution.

A twenty-second aspect, which is a method of making an aqueous cellulosic binder, the method comprising contacting modified cellulose with water, and optionally an electrolyte to form an aqueous cellulosic binder; wherein the modified cellulose comprises CMC and/or sodium CMC; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

A twenty-third aspect, which is the method of the twenty-second aspect, wherein the aqueous cellulosic binder comprises the modified cellulose in an amount of from about 0.1 wt. % to about 50 wt. %.

A twenty-fourth aspect, which is the method of any one of the twenty-second and the twenty-third aspects, wherein contacting modified cellulose with water, and optionally an electrolyte further comprises mixing, agitating, stirring, shaking, sonicating, or combinations thereof.

A twenty-fifth aspect, which is the method of any one of the twenty-second through the twenty-fourth aspects further comprising (i) contacting modified cellulose with water, and optionally an electrolyte to form a modified cellulose solution; and (ii) contacting at least a portion of the modified cellulose solution with a binder modifier to form the aqueous cellulosic binder, wherein the binder modifier comprises a crosslinking agent and/or a wet strength agent; wherein the crosslinking agent comprises a carboxylic acid having two or more carboxyl groups; wherein the wet strength agent comprises at least one reactive functional group selected from the group consisting of a halide group, a chloride group, a fluoride group, a hydroxyl group, and combinations thereof, and wherein the aqueous cellulosic binder is characterized by a weight ratio of binder modifier to modified cellulose of from about 1:2 to about 1:1,000.

A twenty-sixth aspect, which is the method of the twenty-fifth aspect, wherein the step (ii) of contacting at least a portion of the modified cellulose solution with a binder modifier further comprises mixing, agitating, stirring, shaking, sonicating, or combinations thereof.

A twenty-seventh aspect, which is the method of any one of the twenty-second through the twenty-sixth aspects further comprising contacting the aqueous cellulosic binder with an additive selected from the group consisting of a softening agent, an electrolyte, a pigment color, and combinations thereof.

A twenty-eighth aspect, which is the method of the twenty-seventh aspect, wherein contacting the aqueous cellulosic binder with an additive further comprises mixing, agitating, stirring, shaking, sonicating, or combinations thereof.

A twenty-ninth aspect, which is a method of making an aqueous cellulosic binder, the method comprising (a) contacting modified cellulose with water to form a modified cellulose solution, wherein the modified cellulose comprises CMC and/or sodium CMC; and (b) contacting at least a portion of the modified cellulose solution with a binder modifier to form the aqueous cellulosic binder; wherein the binder modifier comprises a crosslinking agent and/or a wet strength agent; wherein the crosslinking agent comprises a carboxylic acid having two or more carboxyl groups; wherein the wet strength agent comprises at least one reactive functional group selected from the group consisting of a halide group, a chloride group, a fluoride group, a hydroxyl group, and combinations thereof, and wherein the aqueous cellulosic binder is characterized by a weight ratio of binder modifier to modified cellulose of from about 1:2 to about 1:1,000.

A thirtieth aspect, which is the method of the twenty-ninth aspect, wherein the modified cellulose solution comprises the modified cellulose in an amount of from about 0.1 wt. % to about 50 wt. %.

A thirty-first aspect, which is the method of any one of the twenty-ninth and the thirtieth aspects, wherein the step (a) of contacting modified cellulose with water further comprises mixing, agitating, stirring, shaking, sonicating, or combinations thereof.

A thirty-second aspect, which is the method of any one of the twenty-ninth through the thirty-first aspects, wherein the step (b) of contacting at least a portion of the modified cellulose solution with a binder modifier further comprises mixing, agitating, stirring, shaking, sonicating, or combinations thereof.

A thirty-third aspect, which is the method of the thirty-second aspect, wherein the binder modifier comprises a crosslinking agent.

A thirty-fourth aspect, which is the method of the thirty-second aspect, wherein the binder modifier comprises a wet strength agent.

A thirty-fifth aspect, which is the method of any one of the twenty-ninth through the thirty-fourth aspects further comprising contacting the aqueous cellulosic binder with an additive selected from the group consisting of a softening agent, an electrolyte, a pigment color, and combinations thereof.

A thirty-sixth aspect, which is the method of the thirty-fifth aspect, wherein contacting the aqueous cellulosic binder with an additive further comprises mixing, agitating, stirring, shaking, sonicating, or combinations thereof.

A thirty-seventh aspect, which is a method of making a nonwoven fabric, the method comprising (a) forming a plurality of fibers into a fiber web; (b) contacting at least a portion of the fiber web with an aqueous cellulosic binder to form a binder impregnated fiber web; wherein the aqueous cellulosic binder comprises modified cellulose, water, and optionally an electrolyte; wherein the aqueous cellulosic binder is characterized by a weight ratio of water to modified cellulose of from about 99.9:0.1 to about 1,000:500; wherein the modified cellulose comprises CMC and/or sodium CMC; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, and (c) curing the binder impregnated fiber web to form the nonwoven fabric.

A thirty-eighth aspect, which is the method of the thirty-seventh aspect, wherein the nonwoven fabric comprises a cured cellulosic binder, and wherein the cured cellulosic binder comprises at least a portion of the modified cellulose of the aqueous cellulosic binder and optionally at least a portion of the electrolyte of the aqueous cellulosic binder.

A thirty-ninth aspect, which is the method of any one of the thirty-seventh and the thirty-eighth aspects, wherein the step (a) of forming a plurality of fibers into a fiber web is a dry laid process.

A fortieth aspect, which is the method of the thirty-ninth aspect, wherein the dry laid process comprises an airlaid process.

A forty-first aspect, which is the method of any one of the thirty-seventh and the thirty-eighth aspects, wherein the step (a) of forming a plurality of fibers into a fiber web can comprise a process selected from the group consisting of an airlaid process, a spunlaid process, and a wet laid process.

A forty-second aspect, which is the method of any one of the thirty-seventh through the forty-first aspects, wherein the plurality of fibers comprises natural fibers, synthetic fibers, or both.

A forty-third aspect, which is the method of the forty-second aspect, wherein the synthetic fibers comprise monocomponent fibers, bicomponent fibers, multicomponent fibers, or combinations thereof.

A forty-fourth aspect, which is the method of any one of the thirty-seventh through the forty-third aspects, wherein the step (b) of contacting the fiber web with a cellulosic binder comprises spraying the aqueous cellulosic binder onto the fiber web.

A forty-fifth aspect, which is the method of any one of the thirty-seventh through the forty-fourth aspects, wherein the fiber web and the aqueous cellulosic binder are contacted at a fabric to liquor ratio of from about 1:0.01 to about 1:20, wherein the fabric to liquor ratio is a mass to volume ratio expressed in kg fiber web to liters of aqueous cellulosic binder.

A forty-sixth aspect, which is the method of any one of the thirty-seventh through the forty-fifth aspects, wherein the step (c) of curing the binder impregnated fiber web comprises heating the binder impregnated fiber web to a temperature of from about 110° C. to about 220° C.

A forty-seventh aspect, which is the method of the forty-third aspect, wherein the step (c) of curing the binder impregnated fiber web comprises chemical and thermal bonding, wherein the bicomponent fibers comprise a core and a sheath surrounding the core, and wherein at least a portion of the sheath melts during the thermal bonding and provides for further bonding of the fiber web.

A forty-eighth aspect, which is the method of the forty-seventh aspect, wherein the thermal bonding comprises calendering, through-air thermal bonding, radiant heat bonding, sonic bonding, or combinations thereof.

A forty-ninth aspect, which a method of making a nonwoven fabric, the method comprising (a) forming a plurality of fibers into a fiber web; (b) contacting at least a portion of the fiber web with an aqueous cellulosic binder to form a binder impregnated fiber web; wherein the aqueous cellulosic binder comprises modified cellulose, a binder modifier, and water; wherein the binder modifier comprises a crosslinking agent and/or a wet strength agent; wherein the aqueous cellulosic binder is characterized by a weight ratio of water to modified cellulose of from about 99.9:0.1 to about 1,000:500; wherein the aqueous cellulosic binder is characterized by a weight ratio of natural binder to modified cellulose of from about 1:2 to about 1:1,000; wherein the modified cellulose comprises CMC and/or sodium CMC; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof; and (c) curing the binder impregnated fiber web to form the nonwoven fabric.

A fiftieth aspect, which is the method of the forty-ninth aspect, wherein the nonwoven fabric comprises a cured cellulosic binder, and wherein the cured cellulosic binder comprises at least a portion of the modified cellulose of the aqueous cellulosic binder and at least a portion of the binder modifier of the aqueous cellulosic binder.

A fifty-first aspect, which is the method of the fiftieth aspect, wherein the binder modifier comprises a crosslinking agent, and wherein the cured cellulosic binder comprises at least a portion of the crosslinking agent of the aqueous cellulosic binder.

A fifty-second aspect, which is the method of the fiftieth aspect, wherein the binder modifier comprises a wet strength agent, and wherein the cured cellulosic binder comprises at least a portion of the wet strength agent of the aqueous cellulosic binder.

A fifty-third aspect, which is the method of any one of the forty-ninth through the fifty-second aspects, wherein the step (a) of forming a plurality of fibers into a fiber web is a dry laid process.

A fifty-fourth aspect, which is the method of the fifty-third aspect, wherein the dry laid process comprises an airlaid process.

A fifty-fifth aspect, which is the method of any one of the forty-ninth through the fifty-second aspects, wherein the step (a) of forming a plurality of fibers into a fiber web can comprise a process selected from the group consisting of an airlaid process, a spunlaid process, and a wet laid process.

A fifty-sixth aspect, which is the method of any one of the forty-ninth through the fifty-fifth aspects, wherein the plurality of fibers comprises natural fibers, synthetic fibers, or both.

A fifty-seventh aspect, which is the method of the fifty-sixth aspect, wherein the synthetic fibers comprise monocomponent fibers, bicomponent fibers, multicomponent fibers, or combinations thereof.

A fifty-eighth aspect, which is the method of any one of the forty-ninth through the fifty-seventh aspects, wherein the step (b) of contacting the fiber web with a cellulosic binder comprises spraying the aqueous cellulosic binder onto the fiber web.

A fifty-ninth aspect, which is the method of any one of the forty-ninth through the fifty-eighth aspects, wherein the fiber web and the aqueous cellulosic binder are contacted at a fabric to liquor ratio of from about 1:0.01 to about 1:20, wherein the fabric to liquor ratio is a mass to volume ratio expressed in kg fiber web to liters of aqueous cellulosic binder.

A sixtieth aspect, which is the method of any one of the forty-ninth through the fifty-ninth aspects, wherein the step (c) of curing the binder impregnated fiber web comprises heating the binder impregnated fiber web to a temperature of from about 110° C. to about 220° C.

A sixty-first aspect, which is the method of the fifty-seventh aspect, wherein the step (c) of curing the binder impregnated fiber web comprises chemical and thermal bonding, wherein the bicomponent fibers comprise a core and a sheath surrounding the core, and wherein at least a portion of the sheath melts during the thermal bonding and provides for further bonding of the fiber web.

A sixty-second aspect, which is the method of the sixty-first aspect, wherein the thermal bonding comprises calendering, through-air thermal bonding, radiant heat bonding, sonic bonding, or combinations thereof.

A sixty-third aspect, which is a nonwoven fabric comprising a fiber web in an amount of from about 85 wt. % to about 99.9 wt. %, based on the total weight of the nonwoven fabric; and a cured cellulosic binder in an amount of from about 0.1 wt. % to about 15 wt. %, based on the total weight of the nonwoven fabric; wherein the cured cellulosic binder comprises modified cellulose, optionally an electrolyte, and optionally a binder modifier; wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof; wherein the binder modifier comprises a crosslinking agent and/or a wet strength agent; wherein, when the binder modifier is present, the cured cellulosic binder is characterized by a weight ratio of binder modifier to modified cellulose of from about 1:2 to about 1:1,000; wherein the modified cellulose comprises CMC and/or sodium CMC; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

A sixty-fourth aspect, which is the nonwoven fabric of the sixty-third aspect, wherein the fiber web comprises natural fibers, synthetic fibers, or both.

A sixty-fifth aspect, which is the nonwoven fabric of the sixty-fourth aspect, wherein the natural fibers comprise cellulosic fibers, and wherein the nonwoven fabric is biodegradable.

A sixty-sixth aspect, which is the nonwoven fabric of any one of the sixty-fourth and the sixty-fifth aspects, wherein the natural fibers comprise cellulosic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E.

A sixty-seventh aspect, which is the nonwoven fabric of any one of the sixty-third through the sixty-sixth aspects, wherein the fiber web comprises natural fibers in an amount of from about 50 wt. % to about 90 wt. %, and bicomponent fibers in an amount of from about 10 wt. % to about 50 wt. %, based on the total weight of the fiber web.

A sixty-eighth aspect, which is the nonwoven fabric of the sixty-seventh aspect, wherein the bicomponent fibers have a partially drawn core.

A sixty-ninth aspect, which is the nonwoven fabric of any one of the sixty-third through the sixty-eighth aspects, wherein the nonwoven fabric comprises the cured cellulosic binder in an amount of from about 0.1 g/m² to about 10 g/m², based on the surface area of the nonwoven fabric.

A seventieth aspect, which is the nonwoven fabric of any one of the sixty-third through the sixty-ninth aspects, wherein the nonwoven fabric is characterized by a dry tensile strength measured in the machine direction of equal to or greater than about 1,100 grams per linear inch (gli), as determined in accordance with EDANA 20.2-89.

A seventy-first aspect, which is the nonwoven fabric of any one of the sixty-third through the seventieth aspects, wherein the nonwoven fabric is characterized by a dry tensile strength measured in the machine direction which is increased by equal to or greater than about 25% when compared to a dry tensile strength measured in the machine direction of an otherwise similar nonwoven fabric that has been treated with a latex-based binder without modified cellulose, and wherein the tensile strength is determined in accordance with EDANA 20.2-89.

A seventy-second aspect, which is the nonwoven fabric of any one of the sixty-third through the seventy-first aspects, wherein the nonwoven fabric treated with 2.5 wt. % cellulosic binder is characterized by a dry tensile strength measured in the machine direction which is increased by equal to or greater than about 10% when compared to a dry tensile strength measured in the machine direction of an otherwise similar nonwoven fabric that has been treated with 12 wt. % of a latex-based binder without modified cellulose, and wherein the tensile strength is determined in accordance with EDANA 20.2-89.

A seventy-third aspect, which is the nonwoven fabric of any one of the sixty-third through the seventy-second aspects, wherein the nonwoven fabric is characterized by a water wet tensile strength measured in the cross direction of less than about 750 grams per linear inch (gli), as determined in accordance with EDANA 20.2-89.

A seventy-fourth aspect, which is the nonwoven fabric of any one of the sixty-third through the seventy-third aspects, wherein the nonwoven fabric is characterized by a water wet tensile strength measured in the cross direction of less than about 400 grams per linear inch (gli), as determined in accordance with EDANA 20.2-89.

A seventy-fifth aspect, which is the nonwoven fabric of any one of the sixty-third through the seventy-fourth aspects, wherein the nonwoven fabric is characterized by a water wet tensile strength measured in the cross direction of less than about 170 grams per linear inch (gli), as determined in accordance with EDANA 20.2-89.

A seventy-sixth aspect, which is the nonwoven fabric of any one of the sixty-third through the seventy-fifth aspects, wherein the nonwoven fabric is characterized by a water wet tensile strength measured in the cross direction which is decreased by equal to or greater than about 25% when compared to a water wet tensile strength measured in the cross direction of an otherwise similar nonwoven fabric that has been treated with a latex-based binder without modified cellulose, and wherein the tensile strength is determined in accordance with EDANA 20.2-89.

A seventy-seventh aspect, which is the nonwoven fabric of any one of the sixty-third through the seventy-sixth aspects, wherein the nonwoven fabric is characterized by a mineral oil wet tensile strength measured in the machine direction of equal to or greater than about 1,200 grams per linear inch (gli), as determined in accordance with EDANA 20.2-89.

A seventy-eighth aspect, which is the nonwoven fabric of any one of the sixty-third through the seventy-seventh aspects, wherein the nonwoven fabric is characterized by a mineral oil wet tensile strength measured in the machine direction which is increased by equal to or greater than about 25% when compared to a mineral oil wet tensile strength measured in the machine direction of an otherwise similar nonwoven fabric that has been treated with a latex-based binder without modified cellulose, and wherein the tensile strength is determined in accordance with EDANA 20.2-89.

A seventy-ninth aspect, which is the nonwoven fabric of any one of the sixty-third through the seventy-eighth aspects, wherein the nonwoven fabric is characterized by a dust level of less than about 5 wt. %, based on the total weight of the nonwoven fabric.

An eightieth aspect, which is the nonwoven fabric of any one of the sixty-third through the seventy-ninth aspects, wherein the fiber web comprises natural fibers, and wherein the nonwoven fabric is characterized by a dust level which is decreased by equal to or greater than about 99% when compared to a dust level of an otherwise similar nonwoven fabric that has not been treated with a binder.

An eighty-first aspect, which is the nonwoven fabric of the eightieth aspect, wherein the fiber web excludes synthetic fibers.

An eighty-second aspect, which is the nonwoven fabric of any one of the sixty-third through the eighty-first aspects, wherein the nonwoven fabric is characterized by a dust level which is decreased by equal to or greater than about 40% when compared to a dust level of an otherwise similar nonwoven fabric that that has been treated with a latex-based binder without modified cellulose.

An eighty-third aspect, which is the nonwoven fabric of any one of the sixty-third through the eighty-second aspects, wherein the nonwoven fabric is characterized by a caliper of equal to or greater than about 0.1 mm, as determined in accordance with EDANA 30.5-99.

An eighty-fourth aspect, which is the nonwoven fabric of any one of the sixty-third through the eighty-third aspects, wherein the nonwoven fabric is characterized by a caliper which is increased by equal to or greater than about 10% when compared to a caliper of an otherwise similar nonwoven fabric that has been treated with a latex-based binder without modified cellulose, as determined in accordance with EDANA 30.5-99.

An eighty-fifth aspect, which is the nonwoven fabric of any one of the sixty-third through the eighty-fourth aspects, wherein the nonwoven fabric is characterized by a water absorbency of equal to or greater than about 5 grams of water per gram of nonwoven fabric (g/gm), as determined in accordance with EDANA 10.3-99.

An eighty-sixth aspect, which is the nonwoven fabric of any one of the sixty-third through the eighty-fifth aspects, wherein the nonwoven fabric is characterized by a water absorbency which is increased by equal to or greater than about 50% when compared to a water absorbency of an otherwise similar nonwoven fabric that has been treated with a latex-based binder without modified cellulose, and wherein the water absorbency is determined in accordance with EDANA 10.3-99.

An eighty-seventh aspect, which is the nonwoven fabric of any one of the sixty-third through the eighty-sixth aspects, wherein the nonwoven fabric treated with 2.5 wt. % cellulosic binder is characterized by a water absorbency which is increased by equal to or greater than about 50% when compared to a water absorbency of an otherwise similar nonwoven fabric that has been treated with 12 wt. % of a latex-based binder without modified cellulose, and wherein the water absorbency is determined in accordance with EDANA 10.3-99.

An eighty-eighth aspect, which is the nonwoven fabric of any one of the sixty-third through the eighty-seventh aspects, wherein the nonwoven fabric is characterized by a mineral oil absorbency of equal to or greater than about 5 grams of mineral oil per gram of nonwoven fabric (g/gm), as determined in accordance with NWSP 010.1.R0 (15).

An eighty-ninth aspect, which is the nonwoven fabric of any one of the sixty-third through the eighty-eighth aspects, wherein the nonwoven fabric is characterized by a mineral oil absorbency which is increased by equal to or greater than about 25% when compared to a mineral oil absorbency of an otherwise similar nonwoven fabric that has been treated with a latex-based binder without modified cellulose, and wherein the mineral oil absorbency is determined in accordance with NWSP 010.1.R0 (15).

A ninetieth aspect, which is the nonwoven fabric of any one of the sixty-third through the eighty-ninth aspects, wherein the nonwoven fabric treated with 2.5 wt. % cellulosic binder is characterized by a mineral oil absorbency which is increased by equal to or greater than about 40% when compared to a mineral oil absorbency of an otherwise similar nonwoven fabric that has been treated with 12 wt. % of a latex-based binder without modified cellulose, and wherein the mineral oil absorbency is determined in accordance with NWSP 010.1.R0 (15).

A ninety-first aspect, which is the nonwoven fabric of any one of the sixty-third through the ninetieth aspects, wherein the nonwoven fabric is characterized by a dispersion time in water of less than about 10 seconds, wherein the dispersion time is determined via a slosh box tester in accordance with GD3 INDA/EDANA.

A ninety-second aspect, which is the nonwoven fabric of the ninety-first aspect, wherein the dispersion time in water increases with increasing the amount of crosslinking agent in the cured cellulosic binder.

A ninety-third aspect, which is the nonwoven fabric of any one of the sixty-third through the ninetieth aspects, wherein the cured cellulosic binder comprises a wet strength agent, and wherein the nonwoven fabric is characterized by no dispersion, and wherein dispersion is determined via a slosh box tester in accordance with GD3 INDA/EDANA; wherein the wet strength agent comprises at least one reactive functional group selected from the group consisting of a halide group, a chloride group, a fluoride group, a hydroxyl group, and combinations thereof.

A ninety-fourth aspect, which is the nonwoven fabric of any one of the sixty-third through the ninety-third aspects, wherein the cured cellulosic binder comprises modified cellulose without the binder modifier, and wherein the nonwoven fabric is characterized by an isopropanol wet tensile strength measured in the cross direction of equal to or greater than about 750 grams per linear inch (gli), as determined in accordance with EDANA 20.2-89.

A ninety-fifth aspect, which is the nonwoven fabric of any one of the sixty-third through the ninety-fourth aspects, wherein the cured cellulosic binder comprises modified cellulose without the binder modifier, and wherein the nonwoven fabric is characterized by an isopropanol wet tensile strength measured in the cross direction of equal to or greater than about 900 grams per linear inch (gli), as determined in accordance with EDANA 20.2-89.

A ninety-sixth aspect, which is the nonwoven fabric of any one of the sixty-third through the ninety-fifth aspects, wherein the cured cellulosic binder comprises modified cellulose without the binder modifier, and wherein the nonwoven fabric is characterized by an isopropanol wet tensile strength measured in the cross direction of equal to or greater than about 1,000 grams per linear inch (gli), as determined in accordance with EDANA 20.2-89.

A ninety-seventh aspect, which is the nonwoven fabric of any one of the sixty-third through the ninety-sixth aspects, wherein the cured cellulosic binder comprises modified cellulose without the binder modifier, and wherein the nonwoven fabric is characterized by an emulsion wet tensile strength measured in the cross direction of equal to or greater than about 150 grams per linear inch (gli), as determined in accordance with EDANA 20.2-89; wherein the emulsion comprises water, an electrolyte, and a solvent selected from the group consisting of glycerol, ethylene glycol, polyethylene glycol, propylene glycol, polypropylene glycol, butylene glycol, and combinations thereof; and wherein the nonwoven fabric is contacted with the emulsion at a weight ratio of emulsion to fabric of about 1:2.

A ninety-eighth aspect, which is the nonwoven fabric of any one of the sixty-third through the ninety-seventh aspects, wherein the cured cellulosic binder comprises modified cellulose without the binder modifier, and wherein the nonwoven fabric is characterized by an emulsion wet tensile strength measured in the cross direction of equal to or greater than about 200 grams per linear inch (gli), as determined in accordance with EDANA 20.2-89; wherein the emulsion comprises water, an electrolyte, and a solvent selected from the group consisting of glycerol, ethylene glycol, polyethylene glycol, propylene glycol, polypropylene glycol, butylene glycol, and combinations thereof; and wherein the nonwoven fabric is contacted with the emulsion at a weight ratio of emulsion to fabric of about 1:2.

A ninety-ninth aspect, which is the nonwoven fabric of any one of the sixty-third through the ninety-eighth aspects, wherein the cured cellulosic binder comprises modified cellulose without the binder modifier, and wherein the nonwoven fabric is characterized by an emulsion wet tensile strength measured in the cross direction of equal to or greater than about 250 grams per linear inch (gli), as determined in accordance with EDANA 20.2-89; wherein the emulsion comprises water, an electrolyte, and a solvent selected from the group consisting of glycerol, ethylene glycol, polyethylene glycol, propylene glycol, polypropylene glycol, butylene glycol, and combinations thereof; and wherein the nonwoven fabric is contacted with the emulsion at a weight ratio of emulsion to fabric of about 1:2.

A hundredth aspect, which is the nonwoven fabric of any one of the sixty-third through the ninety-ninth aspects, wherein the nonwoven fabric is characterized by an isopropanol wet tensile strength measured in the cross direction which is increased by equal to or greater than about 200% when compared to an emulsion wet tensile strength measured in the cross direction; wherein the tensile strength is determined in accordance with EDANA 20.2-89; wherein the emulsion comprises water, an electrolyte, and a solvent selected from the group consisting of glycerol, ethylene glycol, polyethylene glycol, propylene glycol, polypropylene glycol, butylene glycol, and combinations thereof; and wherein the nonwoven fabric is contacted with the emulsion at a weight ratio of emulsion to fabric of about 1:2.

A hundred-and-first aspect, which is the nonwoven fabric of any one of the sixty-third through the hundredth aspects, wherein the nonwoven fabric is characterized by an isopropanol wet tensile strength measured in the cross direction which is increased by equal to or greater than about 350% when compared to an emulsion wet tensile strength measured in the cross direction; wherein the tensile strength is determined in accordance with EDANA 20.2-89; wherein the emulsion comprises water, an electrolyte, and a solvent selected from the group consisting of glycerol, ethylene glycol, polyethylene glycol, propylene glycol, polypropylene glycol, butylene glycol, and combinations thereof, and wherein the nonwoven fabric is contacted with the emulsion at a weight ratio of emulsion to fabric of about 1:2.

A hundred-and-second aspect, which is the nonwoven fabric of any one of the sixty-third through the hundred-and-first aspects, wherein the nonwoven fabric further comprises isopropanol, and wherein the nonwoven fabric is antimicrobial, as determined in accordance with ASTM E2315-03(2008) and/or ASTM E1054-08(2013).

A hundred-and-third aspect, which is the nonwoven fabric of any one of the sixty-third through the hundred-and-second aspects, wherein the nonwoven fabric further comprises isopropanol, and wherein the nonwoven fabric is characterized by at least about 99.9% efficacy at killing *E. coli* and/or *S. aureus*, as determined in accordance with ASTM E2315-03(2008) and/or ASTM E1054-08(2013).

A hundred-and-fourth aspect, which is the nonwoven fabric of any one of the sixty-third through the hundred-and-third aspects, wherein the nonwoven fabric further comprises isopropanol, and wherein the nonwoven fabric is characterized by 100% efficacy at killing *E. coli* and/or *S. aureus*, as determined in accordance with ASTM E2315-03 (2008) and/or ASTM E1054-08(2013).

A hundred-and-fifth aspect, which is an article formed from the nonwoven fabric of any one of the sixty-third through the hundred-and-fourth aspects.

A hundred-and-sixth aspect, which is the article of the hundred-and-fifth aspect, wherein the article is selected from the group consisting of wipes, moisturized wipes, tissues, towels, moisturized tissue towels (MTT), double re-creped (DRC) items, seed blankets, agricultural wraps, agricultural blankets, medical drapes, bandages, caps, face masks, surgical scrubs, medical gowns, filters, diapers, padding, packaging, insulation, carpeting, upholstery, fabric dryer sheets, disposable textiles, earphone protection covers, insulation, wall coverings, and combinations thereof.

A hundred-and-seventh aspect, which is the article of any one of the hundred-and-fifth and the hundred-and-sixth aspects, wherein the wipes comprise industrial wipes, disinfection wipes, water flushable wipes, water dispersible wipes, or combinations thereof.

A hundred-and-eighth aspect, which is a nonwoven fibrous material chemically bound with a modified cellulose-based binder, wherein the modified cellulose-based binder comprises CMC and/or sodium CMC crosslinked with citric acid.

A hundred-and-ninth aspect, which is the nonwoven fibrous material of the hundred-and-eighth aspect, wherein the modified cellulose-based binder further comprises a wet strength agent that chemically binds the nonwoven fibrous material and the CMC and/or sodium CMC; wherein the wet strength agent comprises at least one reactive functional group selected from the group consisting of a halide group, a chloride group, a fluoride group, a hydroxyl group, and combinations thereof.

A hundred-and-tenth aspect, which is an aqueous cellulosic binder comprising modified cellulose, water, and optionally an electrolyte; wherein the aqueous cellulosic binder is characterized by a weight ratio of water to modified cellulose of from about 99.9:0.1 to about 1,000:500; wherein, when the electrolyte is present, the aqueous cellulosic binder comprises the electrolyte in an amount of from about 0.1 wt. % to about 10 wt. %; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

A hundred-and-eleventh aspect, which is the aqueous cellulosic binder of the hundred-and-tenth aspect, wherein the aqueous cellulosic binder is a biodegradable sprayable aqueous solution.

A hundred-and-twelfth aspect, which is an aqueous cellulosic binder comprising modified cellulose, a binder modifier, and water; wherein the aqueous cellulosic binder is characterized by a weight ratio of water to modified cellulose of from about 99.9:0.1 to about 1,000:500; wherein the aqueous cellulosic binder is characterized by a weight ratio of binder modifier to modified cellulose of from about 1:2 to about 1:1,000; wherein the modified cellulose comprises CMC and/or sodium CMC; wherein the binder modifier comprises a crosslinking agent, a wet strength agent, or both a crosslinking agent and a wet strength agent; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

A hundred-and-thirteenth aspect, which is the aqueous cellulosic binder of the hundred-and-twelfth aspect, wherein the aqueous cellulosic binder is a biodegradable sprayable aqueous solution.

A hundred-and-fourteenth aspect, which is a cellulosic binder comprising modified cellulose and a binder modifier in a weight ratio of binder modifier to modified cellulose of from about 1:2 to about 1:1,000; wherein the modified cellulose comprises CMC and/or sodium CMC; wherein the binder modifier comprises a crosslinking agent, a wet strength agent, or both a crosslinking agent and a wet strength agent; and wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

A hundred-and-fifteenth aspect, which is the cellulosic binder of the hundred-and-fourteenth aspect further comprising water; wherein the cellulosic binder is characterized by a weight ratio of water to modified cellulose of from about 99.9:0.1 to about 1,000:500; and wherein the cellulosic binder is a biodegradable sprayable aqueous solution.

A hundred-and-sixteenth aspect, which is a method of making an aqueous cellulosic binder, the method comprising (a) contacting modified cellulose with water to form a modified cellulose solution, wherein the modified cellulose comprises CMC and/or sodium CMC; and (b) contacting at least a portion of the modified cellulose solution with an electrolyte to form the aqueous cellulosic binder; wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, and wherein the aqueous cellulosic binder is characterized by a weight ratio of electrolyte to modified cellulose of from about 1:10 to about 1:1,000.

A hundred-and-seventeenth aspect, which is the method of the hundred-and-sixteenth aspect, wherein the modified cellulose solution comprises the modified cellulose in an amount of from about 0.1 wt. % to about 50 wt. %.

A hundred-and-eighteenth aspect, which is a method of making an aqueous cellulosic binder, the method comprising (a) contacting modified cellulose with water to form a modified cellulose solution, wherein the modified cellulose comprises CMC and/or sodium CMC, and wherein the modified cellulose solution comprises the modified cellulose in an amount of from about 0.1 wt. % to about 50 wt. %; and (b) contacting at least a portion of the modified cellulose solution with a binder modifier to form the aqueous cellulosic binder; wherein the binder modifier comprises a crosslinking agent, a wet strength agent, or both a crosslinking agent and a wet strength agent; wherein the crosslinking agent comprises a carboxylic acid having two or more carboxyl groups; wherein the wet strength agent comprises at least one reactive functional group selected from the group consisting of a halide group, a chloride group, a fluoride group, a hydroxyl group, and combinations thereof, and wherein the aqueous cellulosic binder is characterized by a weight ratio of binder modifier to modified cellulose of from about 1:2 to about 1:1,000.

A hundred-and-nineteenth aspect, which is a method of making a nonwoven fabric, the method comprising (a) forming a plurality of fibers into a fiber web; (b) contacting at least a portion of the fiber web with an aqueous cellulosic binder to form a binder impregnated fiber web; wherein the aqueous cellulosic binder comprises modified cellulose, water, and optionally an electrolyte; wherein the aqueous cellulosic binder is characterized by a weight ratio of water to modified cellulose of from about 99.9:0.1 to about 1,000:500; wherein, when the electrolyte is present, the aqueous cellulosic binder comprises the electrolyte in an amount of from about 0.1 wt. % to about 10 wt. %; and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof, and (c) curing the binder impregnated fiber web to form the nonwoven fabric, wherein the nonwoven fabric comprises a cured cellulosic binder, and wherein the cured cellulosic binder comprises at least a portion of the modified cellulose of the aqueous cellulosic binder and at least a portion of the binder modifier of the aqueous cellulosic binder.

A hundred-and-twentieth aspect, which is the method of the hundred-and-nineteenth aspect, wherein the step (a) of forming a plurality of fibers into a fiber web is an airlaid process.

A hundred-and-twenty-first aspect, which is a method of making a nonwoven fabric, the method comprising (a) forming a plurality of fibers into a fiber web; (b) contacting at least a portion of the fiber web with an aqueous cellulosic binder to form a binder impregnated fiber web; wherein the aqueous cellulosic binder comprises modified cellulose, a binder modifier, and water; wherein the aqueous cellulosic binder is characterized by a weight ratio of water to modified cellulose of from about 99.9:0.1 to about 1,000:500; wherein the aqueous cellulosic binder is characterized by a weight ratio of binder modifier to modified cellulose of from about 1:2 to about 1:1,000; wherein the modified cellulose comprises CMC and/or sodium CMC; wherein the binder modifier comprises a crosslinking agent, a wet strength agent, or both a crosslinking agent and a wet strength agent; and wherein the crosslinking agent comprises a carboxylic acid having two or more carboxyl groups; wherein the wet strength agent comprises at least one reactive functional group selected from the group consisting of a halide group, a chloride group, a fluoride group, a hydroxyl group, and combinations thereof, and (c) curing the binder impregnated fiber web to form the nonwoven fabric, wherein the nonwoven fabric comprises a cured cellulosic binder, and wherein the cured cellulosic binder comprises at least a portion of the modified cellulose of the aqueous cellulosic binder and at least a portion of the binder modifier of the aqueous cellulosic binder.

A hundred-and-twenty-second aspect, which is the method of the hundred-and-twenty-first aspect, wherein the step (a) of forming a plurality of fibers into a fiber web is an airlaid process.

A hundred-and-twenty-third aspect, which is a nonwoven fabric comprising a fiber web in an amount of from about 85 wt. % to about 99.9 wt. %, based on the total weight of the nonwoven fabric, wherein the fiber web comprises natural fibers, synthetic fibers, or both natural fibers and synthetic fibers; and a cured cellulosic binder in an amount of from about 0.1 wt. % to about 15 wt. %, based on the total weight of the nonwoven fabric, wherein the cured cellulosic binder comprises modified cellulose and optionally an electrolyte, and wherein the electrolyte comprises NaCl, KCl, $CaCl_2$, $MgCl_2$, $AlCl_3$, $Na_2SO_4$, $Al_2SO_4$, $K_2SO_4$, $CaSO_4$, alum, or combinations thereof.

A hundred-and-twenty-fourth aspect, which is the nonwoven fabric of the hundred-and-twenty-third aspect, wherein the natural fibers comprise cellulosic fibers, and wherein the nonwoven fabric is biodegradable.

A hundred-and-twenty-fifth aspect, which is the nonwoven fabric of any one of the hundred-and-twenty-third and the hundred-and-twenty-fourth aspects, wherein the natural fibers comprise cellulosic fibers, wherein the synthetic fibers comprise naturally-derived fibers, and wherein the nonwoven fabric is biodegradable.

A hundred-and-twenty-sixth aspect, which is the nonwoven fabric of any one of the hundred-and-twenty-third through the hundred-and-twenty-fifth aspects, wherein the natural fibers comprise cellulosic fibers, wherein the synthetic fibers comprise biodegradable synthetic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E.

A hundred-and-twenty-seventh aspect, which is the nonwoven fabric of the hundred-and-twenty-sixth aspect, wherein the biodegradable synthetic fibers comprise polylactic acid (PLA) based polymers, polybutylene succinate (PBS) based polymers, derivatives thereof, or combinations thereof.

A hundred-and-twenty-eighth aspect, which is the nonwoven fabric of the hundred-and-twenty-seventh aspect, wherein the biodegradable synthetic fibers are bicomponent fibers comprising PLA-based polymers and PBS-based polymers.

A hundred-and-twenty-ninth aspect, which is the nonwoven fabric of any one of the hundred-and-twenty-third and the hundred-and-twenty-fourth aspects, wherein the synthetic fibers comprise polyethylene terephthalate (PET), polyethylene (PE), or combinations thereof, and wherein the nonwoven fabric is non-biodegradable.

A hundred-and-thirtieth aspect, which is an article formed from the nonwoven fabric of any one of the hundred-and-twenty-third through the hundred-and-twenty-ninth aspects.

A hundred-and-thirty-first aspect, which is the article of the hundred-and-thirtieth aspect, wherein the article is selected from the group consisting of wipes, moisturized wipes, flushable wipes, dispersible wipes, tissues, towels, moisturized tissue towels (MTT), double re-creped (DRC) items, seed blankets, agricultural wraps, agricultural blankets, medical drapes, bandages, caps, face masks, surgical scrubs, medical gowns, filters, diapers, padding, packaging, insulation, carpeting, upholstery, fabric dryer sheets, disposable textiles, earphone protection covers, insulation, wall coverings, and combinations thereof.

A hundred-and-thirty-second aspect, which is a nonwoven fabric comprising a fiber web in an amount of from about 85 wt. % to about 99.9 wt. %, based on the total weight of the nonwoven fabric, wherein the fiber web comprises natural fibers, synthetic fibers, or both natural fibers and synthetic fibers; and a cured cellulosic binder in an amount of from about 0.1 wt. % to about 15 wt. %, based on the total weight of the nonwoven fabric, wherein the cured cellulosic binder comprises modified cellulose and a binder modifier in a weight ratio of binder modifier to modified cellulose of from about 1:2 to about 1:1,000, wherein the modified cellulose comprises CMC and/or sodium CMC, wherein the binder modifier comprises a crosslinking agent, a wet strength agent, or both a crosslinking agent and a wet strength agent; wherein the crosslinking agent comprises a carboxylic acid having two or more carboxyl groups; and wherein the wet strength agent comprises at least one reactive functional group selected from the group consisting of a halide group, a chloride group, a fluoride group, a hydroxyl group, and combinations thereof.

A hundred-and-thirty-third aspect, which is the nonwoven fabric of the hundred-and-thirty-second aspect, wherein the natural fibers comprise cellulosic fibers, and wherein the nonwoven fabric is biodegradable.

A hundred-and-thirty-fourth aspect, which is the nonwoven fabric of any one of the hundred-and-thirty-second and the hundred-and-thirty-third aspects, wherein the natural fibers comprise cellulosic fibers, wherein the synthetic fibers comprise naturally-derived fibers, and wherein the nonwoven fabric is biodegradable.

A hundred-and-thirty-fifth aspect, which is the nonwoven fabric of any one of the hundred-and-thirty-second through the hundred-and-thirty-fourth aspects, wherein the natural fibers comprise cellulosic fibers, wherein the synthetic fibers comprise biodegradable synthetic fibers, and wherein the nonwoven fabric is characterized by a degree of biodegradability of equal to or greater than about 99%, wherein the degree of biodegradability refers to aerobic biodegradability in soil as determined in accordance with ISO 17556:2003 E.

A hundred-and-thirty-sixth aspect, which is the nonwoven fabric of the hundred-and-thirty-fifth aspect, wherein the biodegradable synthetic fibers comprise polylactic acid (PLA) based polymers, polybutylene succinate (PBS) based polymers, derivatives thereof, or combinations thereof.

A hundred-and-thirty-seventh aspect, which is the nonwoven fabric of the hundred-and-thirty-sixth aspect, wherein the biodegradable synthetic fibers are bicomponent fibers comprising PLA-based polymers and PBS-based polymers.

A hundred-and-thirty-eighth aspect, which is the nonwoven fabric of any one of the hundred-and-thirty-second and the hundred-and-thirty-third aspects, wherein the synthetic fibers comprise polyethylene terephthalate (PET), polyethylene (PE), or combinations thereof, and wherein the nonwoven fabric is non-biodegradable.

A hundred-and-thirty-ninth aspect, which is an article formed from the nonwoven fabric of any one of the hundred-and-thirty-second through the hundred-and-thirty-eighth aspects.

A hundred-and-fortieth aspect, which is the article of the hundred-and-thirty-ninth aspect, wherein the article is selected from the group consisting of wipes, moisturized wipes, flushable wipes, dispersible wipes, tissues, towels, moisturized tissue towels (MTT), double re-creped (DRC) items, seed blankets, agricultural wraps, agricultural blankets, medical drapes, bandages, caps, face masks, surgical scrubs, medical gowns, filters, diapers, padding, packaging, insulation, carpeting, upholstery, fabric dryer sheets, disposable textiles, earphone protection covers, insulation, wall coverings, and combinations thereof.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. An aqueous cellulosic binder comprising a modified cellulose, water, a wet strength agent, an electrolyte and a crosslinking agent; wherein the aqueous cellulosic binder is characterized by a weight ratio of water to modified cellulose of from about 99.9:0.1 to about 1,000:500; wherein a weight ratio of the crosslinking agent to the modified cellulose ranges from about 1:2 to about 1:1,000; wherein the modified cellulose comprises carboxymethylcellulose (CMC) and/or sodium carboxymethylcellulose (sodium CMC); wherein the crosslinking agent comprises a carboxylic acid having two or more carboxyl groups; and wherein the wet strength agent comprises at least one reactive functional group selected from the group consisting of a halide group, a hydroxyl group, and combinations thereof.

2. The aqueous cellulosic binder of claim 1, wherein the aqueous cellulosic binder is a sprayable aqueous solution.

3. The aqueous cellulosic binder of claim 1, wherein the wet strength agent is present in the aqueous cellulosic binder in an amount ranging from about 0.1 wt. % to about 10 wt. %.

4. The aqueous cellulosic binder of claim 1, further comprising a softening agent in an amount ranging from about 0.1 wt. % to about 10 wt. %.

5. The aqueous cellulosic binder of claim 4, wherein the softening agent comprises an anionic surfactant, glycerol, a polyethylene emulsion, ethylene glycol, polyethylene glycol, propylene glycol, polypropylene glycol, butylene glycol, a fatty alcohol ethoxylate, sodium lauryl sulfate, a silicone-based softener, a nanomaterials-based softener, or combinations thereof.

6. The aqueous cellulosic binder of claim 1, wherein the aqueous cellulosic binder is biodegradable.

7. The aqueous cellulosic binder of claim 1, wherein the halide group is a chloride group or a fluoride group.

8. The aqueous cellulosic binder of claim 1, wherein the carboxylic acid having two or more carboxyl groups is citric acid, oxalic acid, malonic acid, succinic acid, glutaric acid, adipic acid, malic acid, or polyacrylic acid.

9. The aqueous cellulosic binder of claim 1, wherein the carboxylic acid having two or more carboxyl groups is citric acid.

10. The aqueous cellulosic binder of claim 1, wherein the aqueous cellulosic binder comprises the modified cellulose in an amount ranging from about 0.1 wt. % to about 50 wt. %, the aqueous cellulosic binder comprises the crosslinking agent in an amount of from about 0.1 wt. % to about 10 wt. %, the aqueous cellulosic binder comprises the wet strength agent in an amount of from about 0.1 wt. % to about 10 wt. %, and the aqueous cellulosic binder comprises the electrolyte in an amount of from about 0.1 wt. % to about 10 wt. %.

11. The aqueous cellulosic binder of claim 1, further comprising an electrolyte in an amount of from about 0.1 wt. % to about 10 wt. %, wherein the electrolyte comprises NaCl, KCl, $CaCl_2$), $MgCl_2$, $AlCl_3$, $Na_2SO_4$, $Al_2SO_4$, $K_2SO_4$, $CaSO_4$, alum, or combinations thereof.

12. A method of making an aqueous cellulosic binder, the method comprising:
  (i) contacting a modified cellulose with water and an electrolyte to form a modified cellulose solution; and
  (ii) contacting at least a portion of the modified cellulose solution with a binder modifier to form the aqueous cellulosic binder, wherein
    the binder modifier comprises a crosslinking agent and/or a wet strength agent, the crosslinking agent comprising a carboxylic acid having two or more carboxyl groups and the wet strength agent comprising at least one reactive functional group selected from the group consisting of a halide group, a hydroxyl group, and combinations thereof,
    the aqueous cellulosic binder is characterized by a weight ratio of binder modifier to modified cellulose ranging from about 1:2 to about 1:1,000,
    the modified cellulose comprises CMC and/or sodium CMC, and
    the electrolyte comprises NaCl, KCl, $CaCl_2$), $MgCl_2$, $AlCl_3$, $Na_2SO_4$, $Al_2SO_4$, $K_2SO_4$, $CaSO_4$, alum, or combinations thereof.

13. The method of claim 12, wherein the binder modifier comprises the crosslinking agent.

14. The method of claim 12, wherein the binder modifier comprises the wet strength agent.

15. The method of claim 12, wherein the binder modifier comprises the crosslinking agent and the wet strength agent.

16. The method of claim 12, wherein the halide group is a chloride group or a fluoride group.

17. The method of claim 12, wherein the aqueous cellulosic binder is characterized by a weight ratio of electrolyte to modified cellulose ranging from about 1:10 to about 1:1,000.

* * * * *